(12) United States Patent
Scheffler et al.

(10) Patent No.: US 9,573,960 B2
(45) Date of Patent: Feb. 21, 2017

(54) GLIOBLASTOMA INHIBITING COMPOUNDS AND THEIR USE

(75) Inventors: Björn Scheffler, Bonn (DE); Martin Glas, Bonn (DE); Matthias Simon, Bonn (DE); Sabine Gogolok, Hagen (DE); Daniel Trageser, Bonn (DE); Roman Reinartz, Bonn (DE); Anja Wieland, Wachtberg (DE)

(73) Assignees: Life & Brain GmbH, Bonn (DE); Rheinische Friedrich-Wilhelms Universitat, Bonn (DE)

(*) Notice: Subject to any disclaimer, the term of this patent is extended or adjusted under 35 U.S.C. 154(b) by 50 days.

(21) Appl. No.: 14/126,512

(22) PCT Filed: Jun. 15, 2012

(86) PCT No.: PCT/EP2012/061485
§ 371 (c)(1),
(2), (4) Date: Mar. 10, 2014

(87) PCT Pub. No.: WO2012/172069
PCT Pub. Date: Dec. 20, 2012

(65) Prior Publication Data
US 2015/0148390 A1    May 28, 2015

Related U.S. Application Data

(60) Provisional application No. 61/497,215, filed on Jun. 15, 2011.

(51) Int. Cl.
| | | |
|---|---|---|
| *C07D 493/06* | (2006.01) |
| *C07D 493/18* | (2006.01) |
| *A61K 31/352* | (2006.01) |
| *G01N 33/574* | (2006.01) |
| *A61K 31/4188* | (2006.01) |

(52) U.S. Cl.
CPC .......... *C07D 493/18* (2013.01); *A61K 31/352* (2013.01); *A61K 31/4188* (2013.01); *C07D 493/06* (2013.01); *G01N 33/57492* (2013.01); *G01N 2333/70596* (2013.01); *G01N 2800/52* (2013.01)

(58) Field of Classification Search
CPC .. C07D 493/06; C07D 493/18; A61K 31/352; G01N 33/574
See application file for complete search history.

(56) References Cited

U.S. PATENT DOCUMENTS

2003/0078291 A1    4/2003   Ihara et al.
2003/0078292 A1    4/2003   Cai et al.

FOREIGN PATENT DOCUMENTS

EP    1300403 A1    4/2003

OTHER PUBLICATIONS

Curley et al., 2009, http://www.ncbi.nlm.nih.gov/pubmed/19816957.*
Lu et al., Cancer Letters 258 (2007), 80-89.*
Peng J Y et al: "Separation of Two New Prenylated Dihydroflavonoids from Dolichos tenuicaulis (Baker) Craib by High-speed Counter-current Chromatography",Chinese Journal of Analytical Chemistry, vol. 35, No. 10, Oct. 1, 2007 (Oct. 1, 2007), pp. 1444-1448, XP022857804, ISSN: 1872-2040, 001: 10. 1016/S1872-2040(07) 60087-5 [retrieved on Oct. 1, 2007] p. 1444; compound 1.
Qiang et al., Inhibition of glioblastoma growth and angiogenesis by gambogic acid: An in vitro and in vivo study, Biochemical Pharmacology, Apr. 2008.

* cited by examiner

*Primary Examiner* — Sun Jae Yoo
(74) *Attorney, Agent, or Firm* — Barnes & Thornburg LLP

(57) ABSTRACT

The present invention relates to glioblastoma inhibiting compounds, in particular gambogic acid amid and derivatives thereof for the treatment of glioblastoma. Moreover, methods for determining whether a treatment with the compounds of the invention is suitable for a patient are disclosed.

11 Claims, 23 Drawing Sheets

(a)

(b)

Figure 14 A (1)
046 - Gambogic Acid
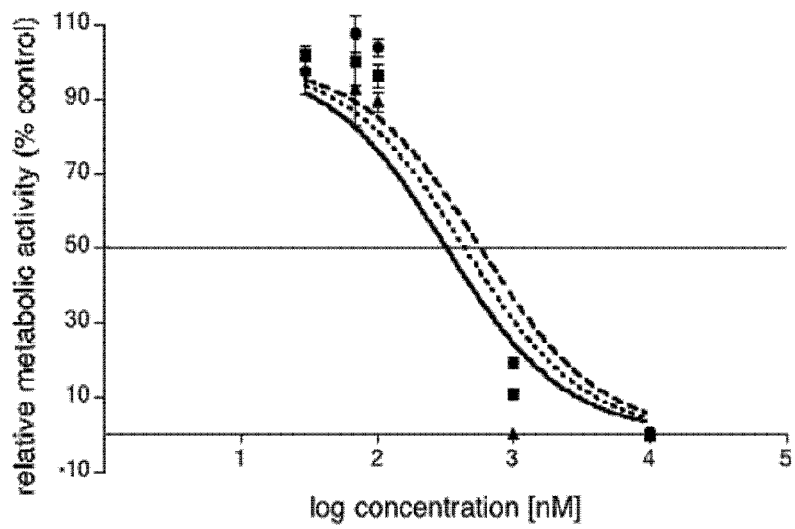
046 - Gambogic acid amide
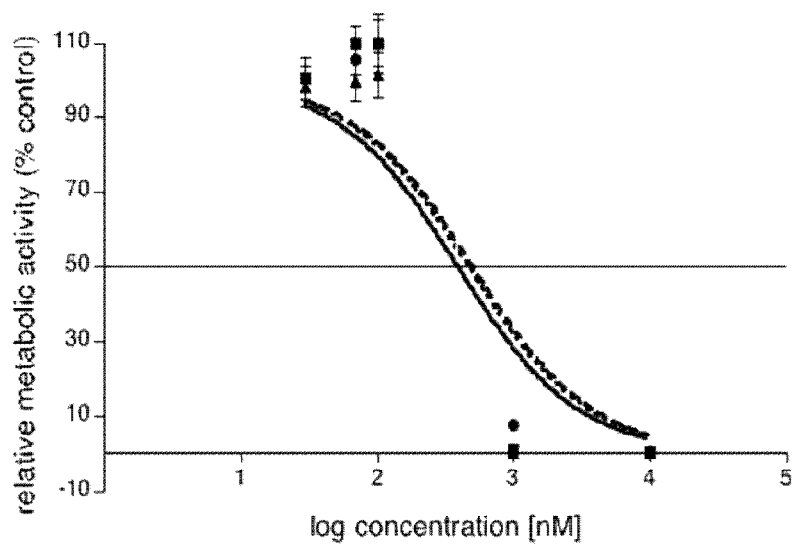

Figure 14 A (2)
\# 106 Gambogic Acid
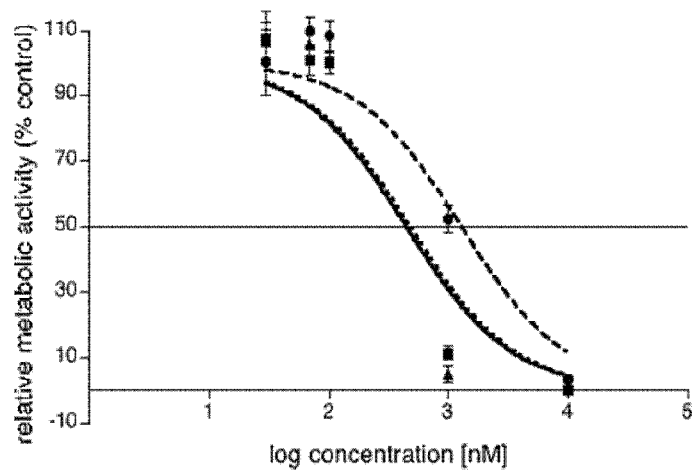
\# 106 Gambogic Acid Amide
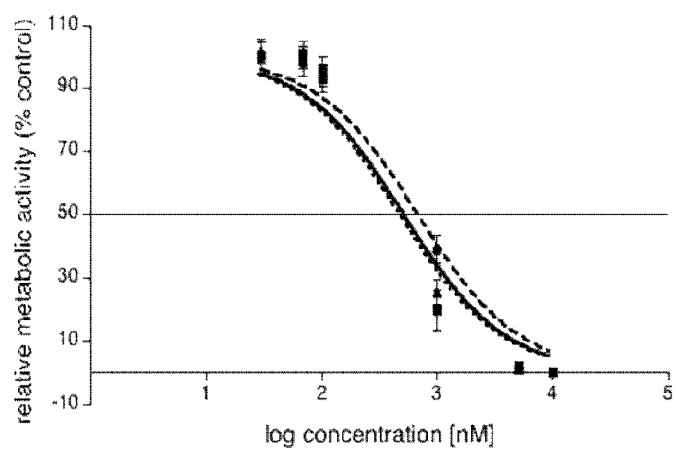

Figure 14 A (3)
\# 138 Gambogic Acid
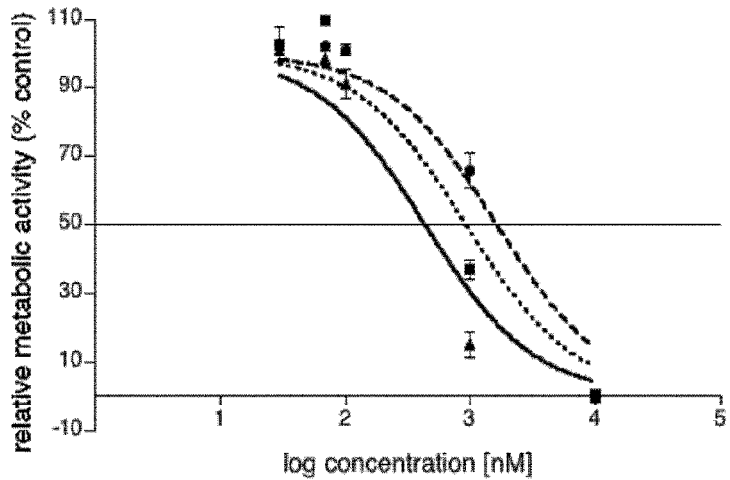
\# 138 Gambogic Acid Amide
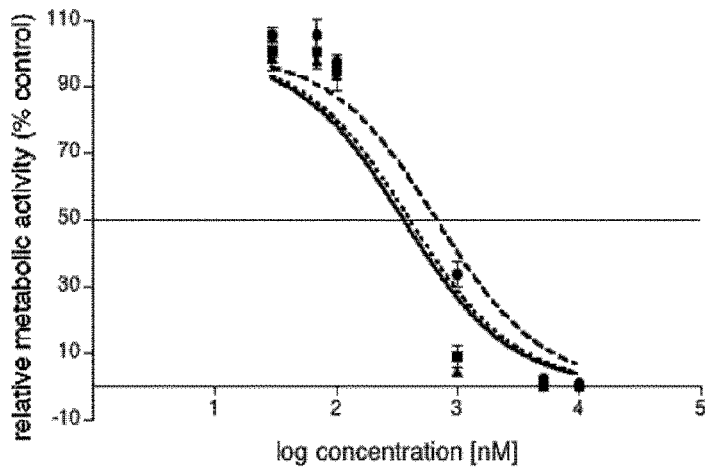
Figure 14 B
| MC50 | 24h | 48h | 144h |
|---|---|---|---|
| 046_GA | 575nM | 441nM | 324nM |
| 046_GAA | 501nM | 470nM | 392nM |
| 106_GA | 1294nM | 481nM | 448nM |
| 106_GAA | 681nM | 474nM | 514nM |
| 138_GA | 1640nM | 929nM | 436nM |
| 138_GAA | 676nM | 405nM | 363nM |

Figure 16 (1)
46 Gambogic Acid
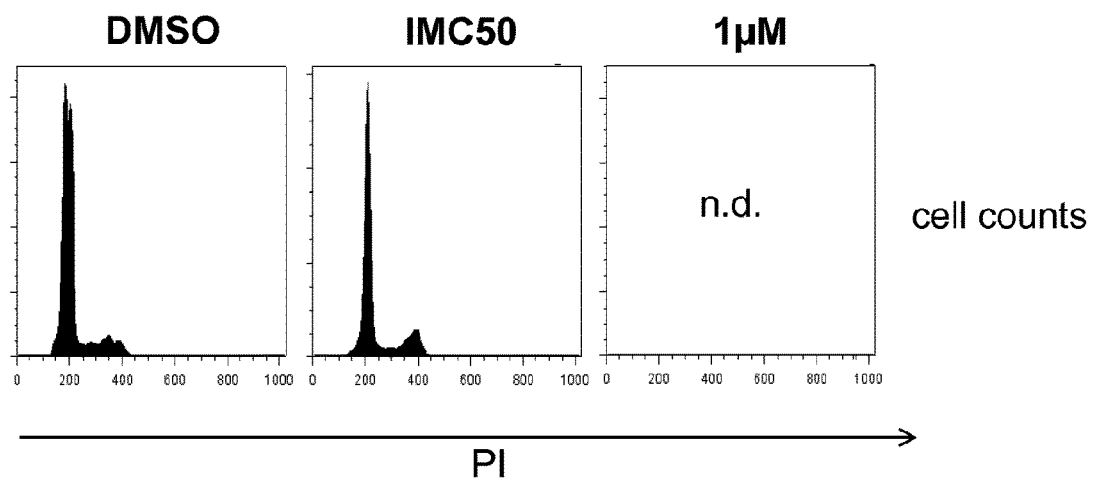
46 Gambogic Acid Amide
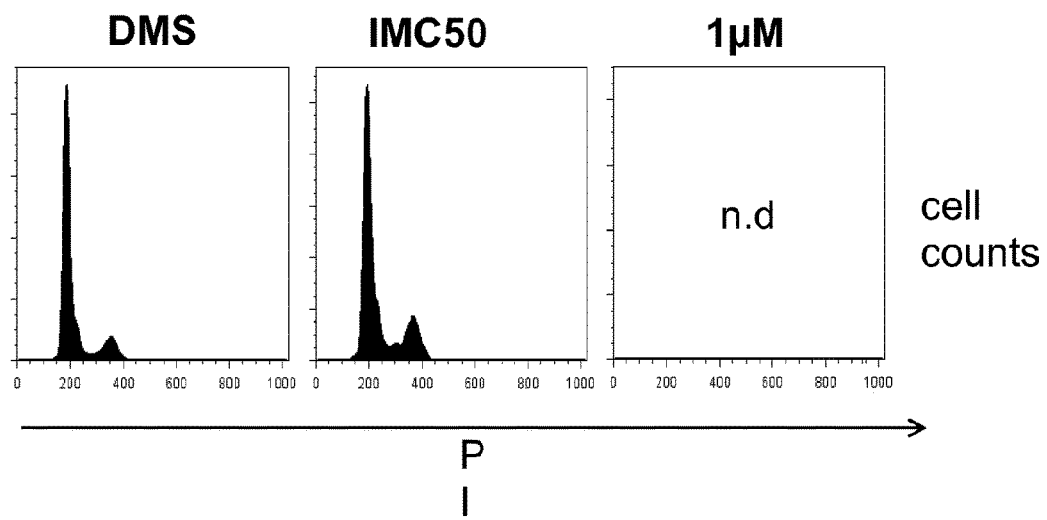

Figure 16 (2)
\# 106 Gambogic Acid
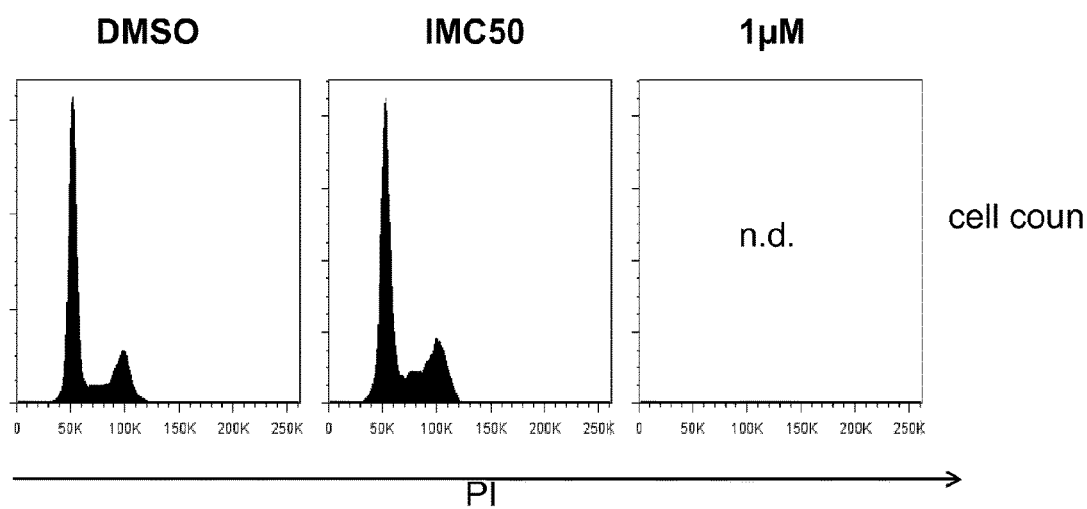
\# 106 Gambogic Acid Amide
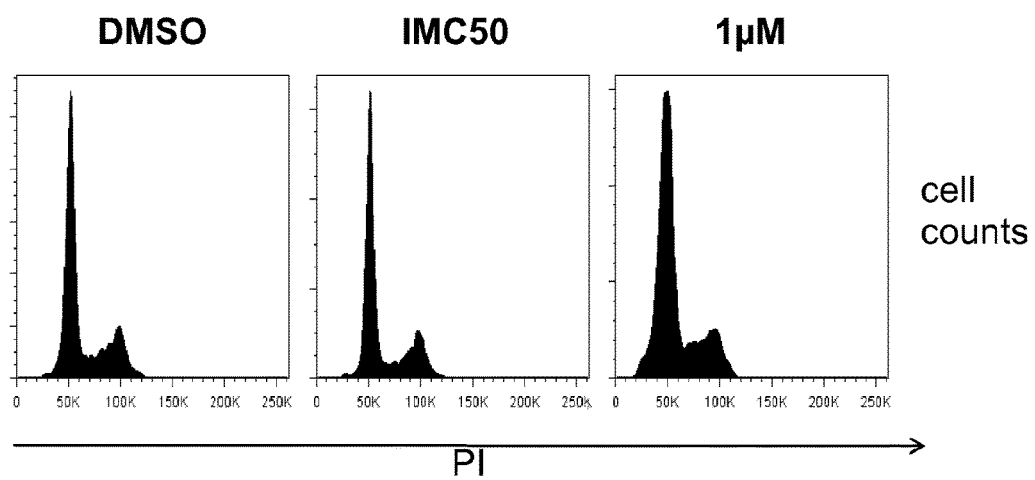

Figure 16 (3)
138 Gambogic Acid
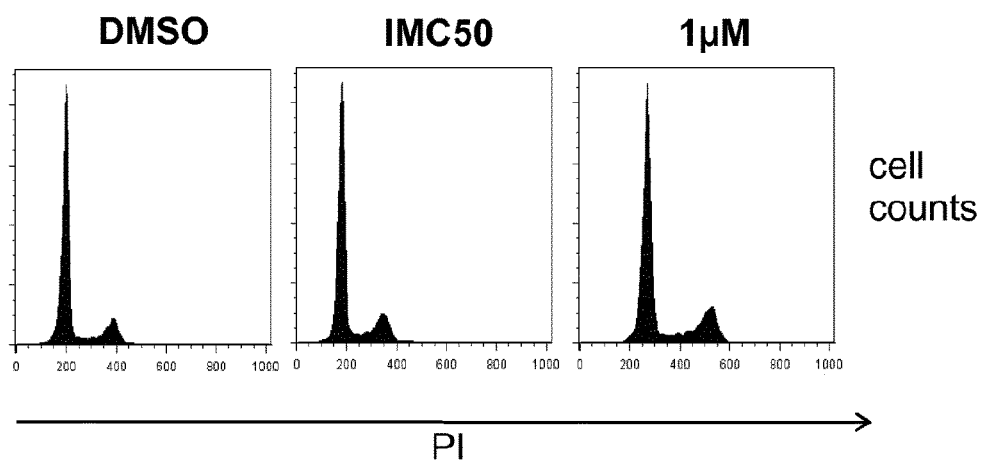
138 Gambogic Acid Amide
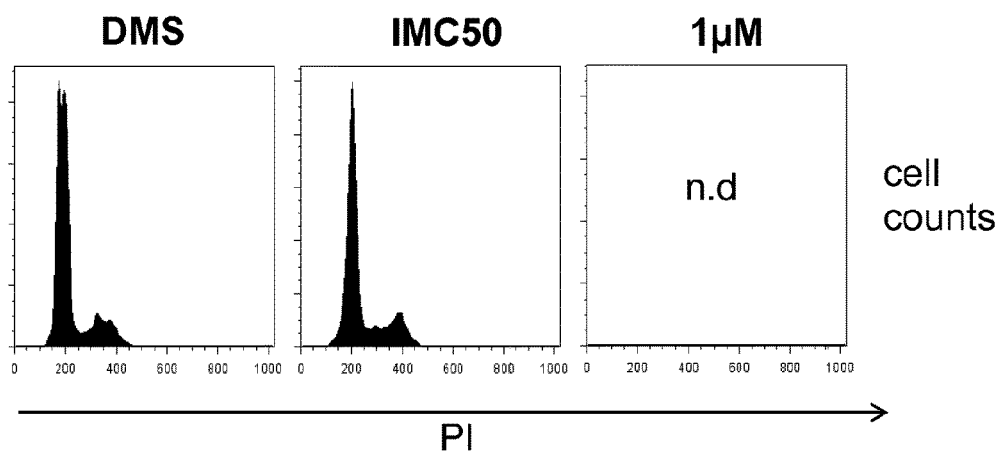

Figure 17
A
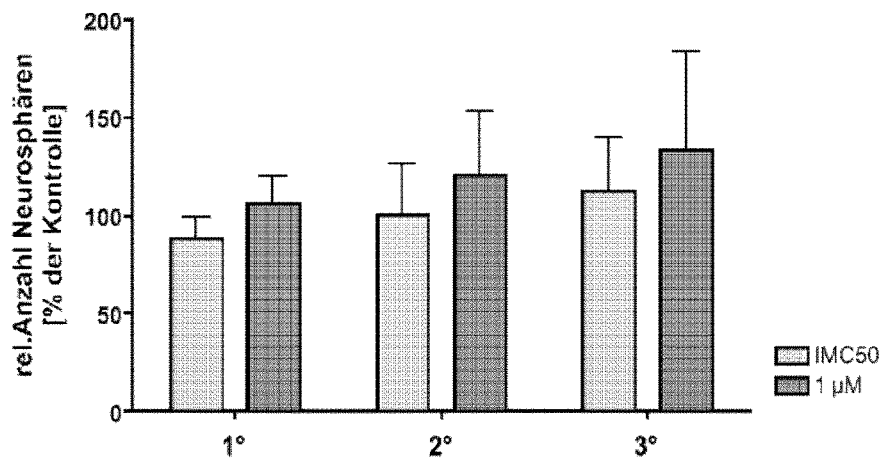
B
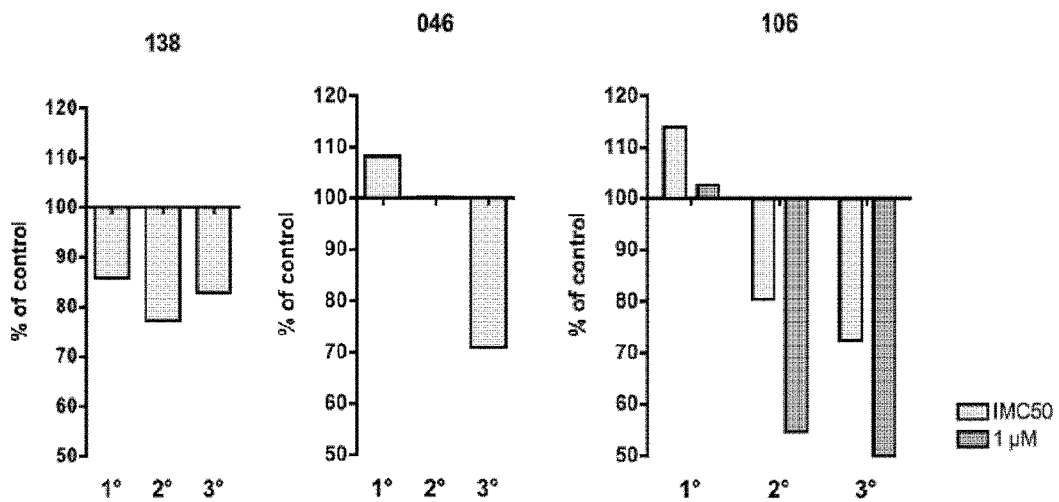

Figure 18
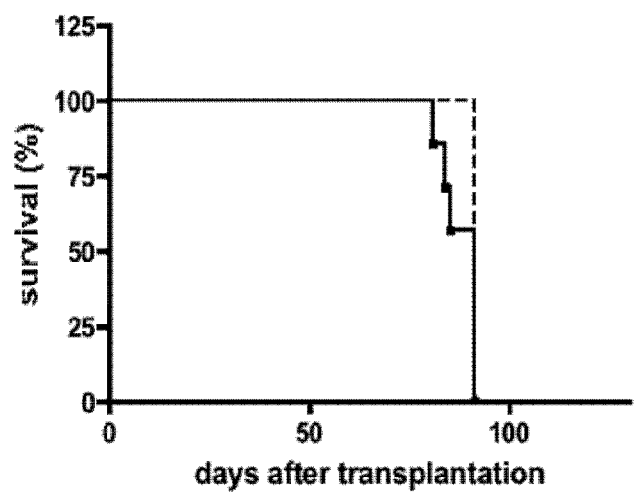
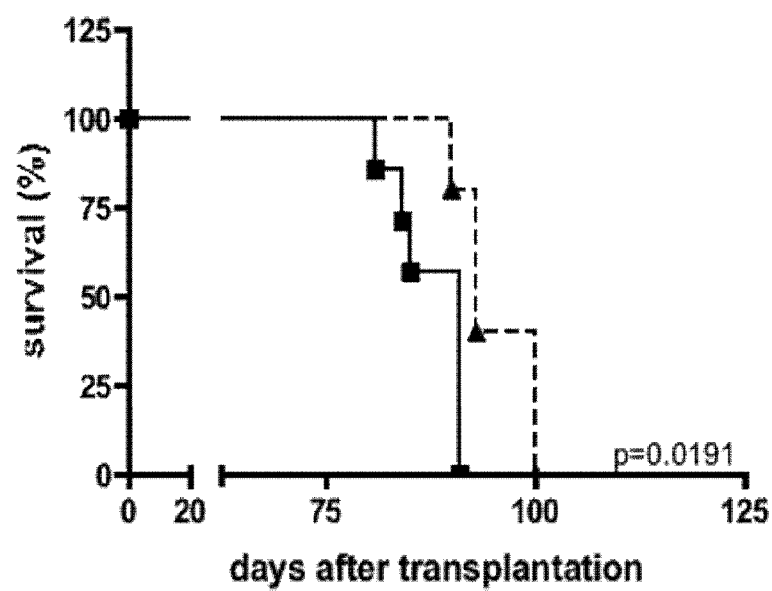

Figure 19 A
Gambogic Acid
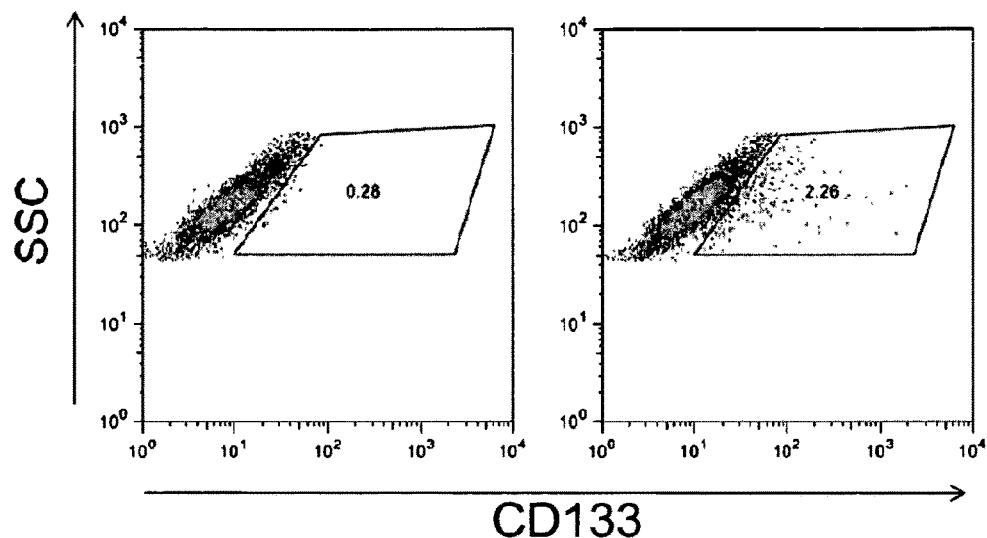
Gambogic Acid Amide
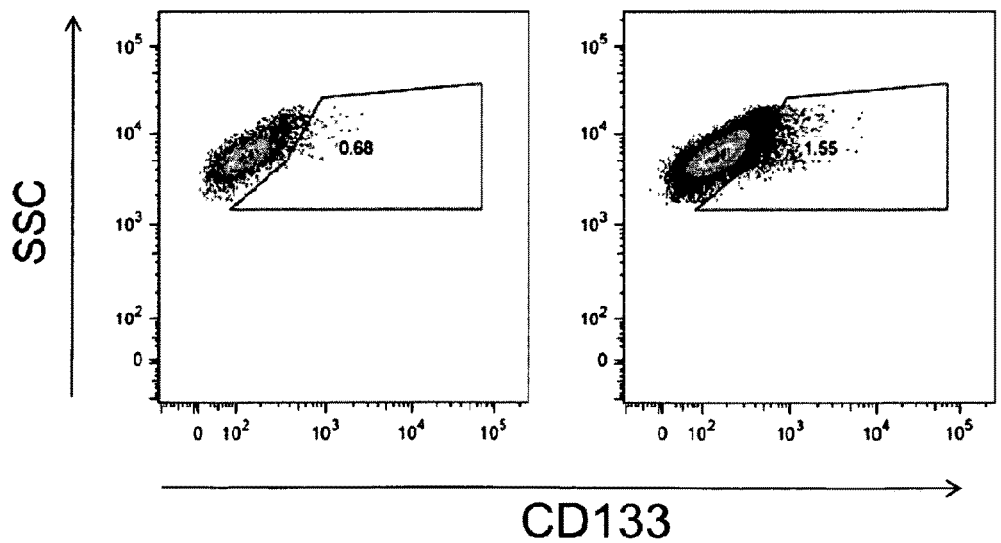

Figure 19 B
B
Gambogic Acid
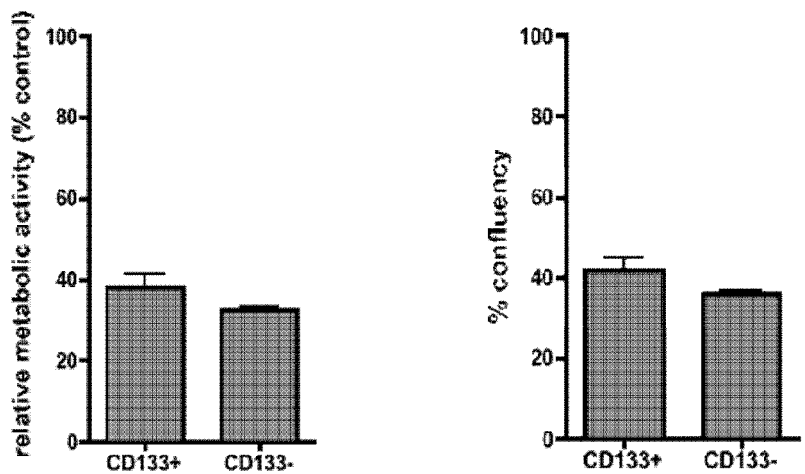
Gambogic Acid Amide
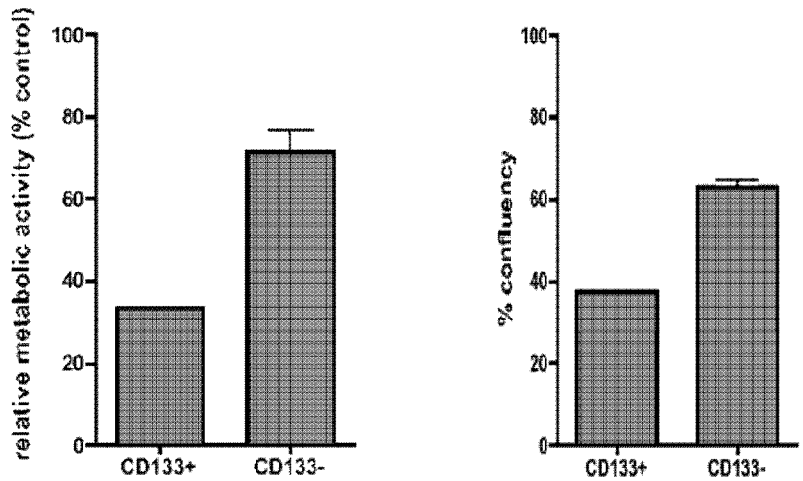

GLIOBLASTOMA INHIBITING COMPOUNDS AND THEIR USE

CROSS-REFERENCE TO RELATED APPLICATIONS:

This application is a US National Phase filing of PCT/EP2012/061485, filed on Jun. 15, 2012, which claims benefit to US 61/497,215, filed on Jun. 15, 2011. The disclosure therein is expressly incorporated entirely by reference.

The present invention relates to glioblastoma inhibiting compounds, in particular gambogic acid amid and derivatives thereof for the treatment of glioblastoma. Moreover, methods for determining whether a treatment with the compounds of the invention is suitable for a patient are disclosed.

BACKGROUND OF THE INVENTION

Glioblastoma (GBM; World Health Organization grade IV glioma) is the most common primary brain tumor in adults. Even with aggressive surgical resection using state-of-the-art preoperative and intraoperative neuroimaging along with recent advances in postsurgical radiotherapy and chemotherapy, the prognosis for GBM patients remains dismal. The median survival rate under the current optimum postsurgical treatment protocol is only 15 months (Stupp et al., 2005). The identification of new candidate therapeutics has thus highest priority. One challenge in defining new therapeutic approaches is the heterogeneity of GBMs. An intra-tumoral heterogeneity is derived from genetic and non-genetic epigenetic causes. Also, an emerging concept proposes that heterogeneous tumor cell phenotypes arise from continuing operation of aberrant and malignant differentiation processes initiated by a small subset of stem-like cells. These stem-like cells have are defined by their capacity (i) of self-renewal, (ii) of tumor initiation and propagation in various xenotransplantation paradigms and (iii) multipotency, i.e. their capacity to differentiate into astrocytes, oligodendrocytes and neurons (Singh et al., 2004). In addition, it is presumed that these cells are resistant to most current radio- and chemotherapies, and it is thought that therapies directed against stem-like cells may improve the dreadful record of current conventional therapies (Dirks, 2008; Chalmers, 2007). Based on this view, it has been begun to adapt in vitro technologies commonly applied in the field of stem cell research to isolate, expand, and to better characterize tumor cells with stem cell characteristics (Pardal et al., 2003, Glas et al., 2010). Cells are propagated as a monolayer culture under adhesive conditions, which may offer significant advantages in comparison to "sphereoid" cultures (Lee et al., 2006; Pollard et al., 2009).

Thus, the problem underlying the present invention can be viewed as the provision of novel compounds for the improved chemotherapy of glioblastoma.

SUMMARY OF THE INVENTION

In a first aspect the present invention relates to a compound according to formula I, II or III

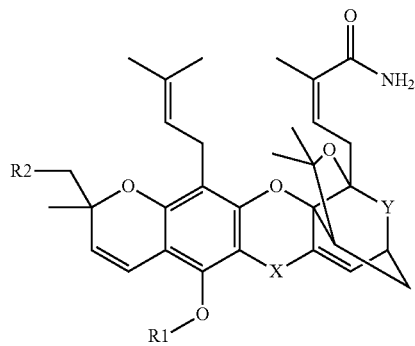
(I)

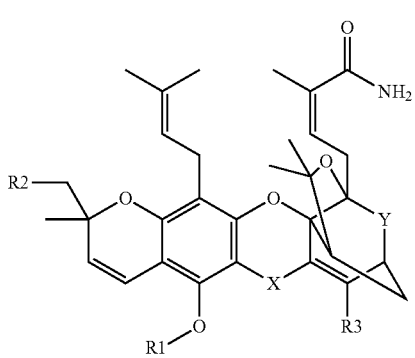
(II)

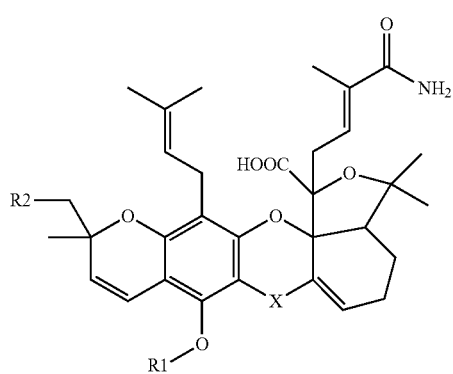
(III)

for use in the treatment of glioblastoma, wherein

X is carbonyl, methylene, hydroxymethinyl, alkoxymethinyl, aminomethinyl, oxime, hydrazone, arylhydrazone or semicarbazone;

Y is carbonyl, methylene, hydroxymethinyl, alkoxymethinyl, aminomethinyl, oxime, a hydrazone, arylhydrazone or semicarbazone;

$R_1$ is hydrogen, substituted alkyl, acyl ($R_aCO$), carbamyl ($R_bR_cNCO$) or sulfonyl ($R_aSO_2$); wherein $R_a$ is hydrogen, substituted lower alkyl, substituted aryl, substituted lower aralkyl group or N-succinimidyl; $R_b$ and $R_c$ are independently hydrogen substituted heteroalkyl, substituted lower alkyl, substituted aryl, substituted heteroaryl or substituted lower aralkyl groups;

$R_2$ is prenyl or hydrogen; and $R_3$ if present, is hydrogen, halogen, hydroxyl, substituted alkyl, cycloalkyl, alkoxy, alkylthio or amino.

In a further aspect the present invention relates to a pharmaceutical composition comprising a compound according to formula I, II or III, wherein X, Y, $R_1$, $R_2$ and $R_3$ have the meaning set out above, for the treatment of glioblastoma.

In a further aspect the present invention relates to a method for determining if treatment with a compound according to formula I, II or III, wherein X, Y, $R_1$, $R_2$ and $R_3$ have the meaning set out above is suitable for a patient comprising the steps of a) determining the expression level of CD133 in a sample of tumor tissue or tumor cells of the patient;
b) comparing the expression level determined in step a) with a reference value; and
c) determining whether treatment with a compound according to formula I, II or III is suitable for a patient based on the result of the comparison of step b), wherein overexpression indicates that said treatment is suitable for the patient.

DETAILED DESCRIPTION OF THE INVENTION

Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In the study underlying the present invention, the improved culturing conditions described in the introduction have been applied to screen primary cultures of 4 patient-specific GBM cells for their metabolic response to an application of various compounds. 31 compounds showed a thorough metabolic response based on AlamarBlue® analysis. The most intriguing anti-GBM compounds (i.e. Gambogic acid amide, Gambogic acid, Pristimerin, Epirubicin hydrochloride, Emetine and Niclosamide) were further validated using pharmacodynamic assays, AnnexinV-analysis of apoptosis, study of growth kinetics, quantification of self-renewing, multipotent CSCs, expression profiling of stem cell markers, and investigation of the particular mode of action. The data indicate that these substances are highly efficient anti-GBM therapeutics.

Thus the problem underlying the present invention is solved by the provision of a compound selected from the group consisting of Gambogic acid amide, Daunorubicine, Gambogic acid, Thimerosal, Mitoxanthrone hydrochloride, Phenylmercuric acetate, Dactinomycin, Pristimerin, Epirubicin hydrochloride, Vincristine sulfate, Emetine, Paclitaxel, 10-Hydroxycamptothecin, Doxorubicine, Colchicine, Camptothecin, Teniposide, Vinblastine sulfate, Mitomycin C, Floxuridine, Ouabain, Ancitabine hydrochloride, Quinacrine hydrochloride, Niclosamide, Amsacrine, Thioguanine, Rotenone, Aklavine hydrochloride, Cytarabine, Methotraxate, and Picropodophyllotoxin for use in the treatment of glioblastoma.

In a preferred embodiment, the compound is a compound according to formula I, II or III,

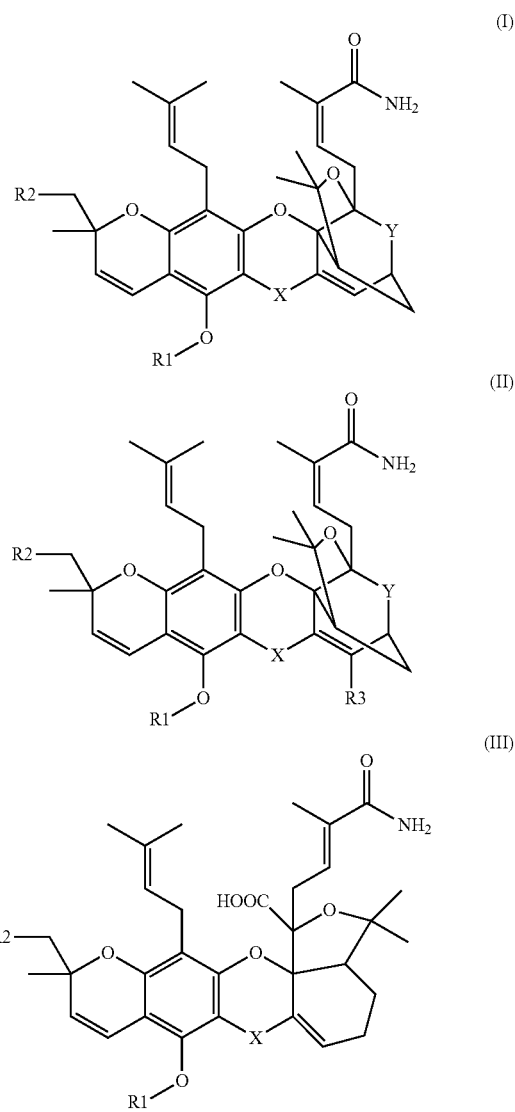

wherein
X is carbonyl, methylene, hydroxymethinyl, alkoxymethinyl, aminomethinyl, oxime, hydrazone, arylhydrazone or semicarbazone, preferably carbonyl;
Y is carbonyl, methylene, hydroxymethinyl, alkoxymethinyl, aminomethinyl, oxime, a hydrazone, arylhydrazone or semicarbazone, preferably carbonyl;
$R_1$ is hydrogen, substituted alkyl, acyl ($R_aCO$—), or carbamyl ($R_bR_cNCO$—); wherein $R_a$ is hydrogen, substituted lower alkyl, substituted aryl, substituted lower aralkyl group or N-succinimidyl; $R_b$ and $R_c$ are independently hydrogen substituted heteroalkyl, substituted lower alkyl, substituted aryl, substituted heteroaryl or substituted lower aralkyl groups, preferably hydrogen;
$R_2$ is prenyl or hydrogen, preferably prenyl; and
$R_3$ is hydrogen, halogen, hydroxyl, substituted alkyl, cycloalkyl, alkoxy, alkylthio or amino, preferably hydrogen or salts thereof.

Alkyl groups are, preferably, straight-chained or branched $C_1$ to $C_{10}$ alkyl groups, more preferably $C_1$ to $C_6$ alkyl groups. Alkyl groups comprising not more than 6 carbon atoms are referred to as "lower alkyl". Preferred alkyl groups comprise methyl, ethyl, propyl, isopropyl, butyl, sec-butyl, tert-butyl, 3-pentyl, hexyl and octyl groups.

Preferred alkoxy groups comprise oxygen substituted by one of the alkyl groups recited above, preferably by methyl, ethyl, propyl, isopropyl, butyl, sec-butyl, tert-butyl, 3-pentyl, hexyl and octyl groups, more preferably methyl.

Preferred alkylthio groups comprise sulphur substituted by one of the alkyl groups recited above, preferably by methyl, ethyl, propyl, isopropyl, butyl, sec-butyl, tert-butyl, 3-pentyl, hexyl and octyl groups, more preferably methyl, sulfoxides and sulfones.

Preferred amino groups comprise —$NH_2$, —$NHR_{11}$, —$NR_{11}R_{12}$, wherein $R_{11}$ and $R_{12}$ are $C_1$ to $C_{10}$ alkyl, preferably selected from the grouped methyl, ethyl, propyl, isopropyl, butyl, sec-butyl, tert -butyl, 3-pentyl, hexyl and octyl groups, most preferably methyl, or cycloalkyl groups or $R_{11}$ and $R_{12}$ are combined with the N to form a ring structure, preferably a 5 to 7 membered ring structure, such as piperidine or $R_{11}$ and $R_{12}$ are combined with the N and another heteroatom to form a saturated, substituted, or partially saturated 5-7-membered heterocyclo group. Preferred heteroatoms include O, N and S.

Preferred substituents of the alkyl groups comprise at least one halogen, hydroxyl, carboxyl, alkoxycarbonyl, amino, nitro, cyano, $C_1$ to $C_6$ acylamino, $C_1$ to $C_6$ aminoacyl, $C_1$ to $C_6$ acyloxy, $C_1$ to $C_6$ alkoxy, aryloxy, alkylthio, $C_6$ to $C_{10}$ aryl, $C_4$ to $C_7$ cycloalkyl, $C_2$ to $C_6$ alkenyl and $C_2$ to $C_6$ alkynyl.

Preferred substituents of the aryl, aralkyl and heteroaryl groups comprise at least one acyl, alkylenedioxy (—$OCH_2O$—), halogen, $C_1$ to $C_6$ haloalkyl, $C_6$ to $C_{10}$ aryl, $C_4$ to $C_7$ cycloalkyl, $C_1$ to $C_6$ alkyl, $C_2$ to $C_6$ alkenyl, $C_2$ to $C_6$ alkynyl, $C_1$ to $C_6$ hydroxyalkyl, nitro, amino, ureido, cyano, $C_1$ to $C_6$ acylamino, thiol, hydroxy, $C_1$ to $C_6$ alkoxy, $C_1$ to $C_6$ acyloxy, azido and carboxy.

Preferred heteroalkyl groups comprise 1 to 10 carbon atoms and 1 to 3 heteroatoms. The heteroalkyl groups may be substituted. Preferred substituents comprise at least one acyl, alkylenedioxy (—$OCH_2O$—), halogen, $C_1$ to $C_6$ haloalkyl, $C_6$ to $C_{10}$ aryl, $C_4$ to $C_7$ cycloalkyl, $C_1$ to $C_6$ alkyl, $C_2$ to $C_6$ alkenyl, $C_2$ to $C_6$ alkynyl, $C_1$ to $C_6$ hydroxyalkyl, nitro, amino, cyano, $C_1$ to $C_6$ acylamino, thiol, hydroxy, $C_1$ to $C_6$ alkoxy, $C_1$ to $C_6$ acyloxy, azido and carboxy.

Preferred aryl groups comprise $C_6$ to $C_{14}$ aryl, more particularly $C_6$ to $C_{10}$ aryl. More preferably, the aryl group is phenyl, naphtyl, phenanthrenyl, anthracenyl, indenyl, azulenyl, bephenyl, biphenylenyl or fluorenyl.

Preferred halogens comprise fluorine, iodine, chlorine and bromine.

Preferred cycloalkyl groups are $C_3$ to $C_8$ cycloalkyl, in particular cyclopentyl, cyclohexyl, cycloheptyl and cyclooctyl. Further preferred are the corresponding cycloalkenyl groups, in particular cyclopentenyl, cyclohexenyl, cycloheptenyl and cyclooctenyl.

Preferred aralkyl groups comprise any of the above-mentioned $C_1$ to $C_{10}$ alkyl groups substituted by any of the above-mentioned $C_6$ to $C_{14}$ aryl groups. Particularly preferred are benzyl, phenethyl and naphtylmethyl.

Preferred heteroaryl groups comprise thienyl, benzo[b]thienyl, naphto[2,3-b]thienyl, thianthrenyl, furanyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phtalzinyl, naphthyridinyl, quinozalinyl, cinnolinyl, pteridinyl, carbazolyl, β-carbolinyl, phenanthridinyl, acrindinyl, permidinyl, phenanthrolinyl, phenazinyl, isothiazolyl, phenothiazonyl, isoxazolyl, furazanyl, phenoxazinyl, 1,4-dihydroquinoxaline-2,3-dione, 7-aminoisocoumarin, pyrido[1,2a]pyrimidin-4-one, 1,2-benzoisoxazol-3-yl, benzimidazolyl, 2-oxindolyl and 2-oxobenzimidazolyl. Preferred substituents of the heteroaryl group comprise at least one heteroaryl, heterocyclo, alkyl, aralkyl, cycloalkyl, alkoxycarbonyl, carbamyl, aryl and $C_1$ to $C_6$-aminoacyl In a more preferred embodiment, the compound is selected from the group consisting of a compound as defined by formula I, wherein $R_1$ is hydrogen, $R_2$ is prenyl, X is carbonyl and Y is carbonyl; a compound as defined by formula II, wherein $R_1$ is hydrogen, $R_2$ is prenyl, $R_3$ is hydrogen X and Y is hydroxymethinyl; a compound as defined by formula II, wherein $R_1$ is hydrogen, $R_2$ is prenyl, X is carbonyl and Y is hydroxymethinyl; a compound as defined by formula I, wherein $R_1$ is acetyl, $R_2$ is prenyl, X is carbonyl and Y is carbonyl; and a compound as defined by formula III, wherein $R_1$ is hydrogen, $R_2$ is prenyl and X is carbonyl.

Preferably the compounds according to formulas (I) and (II) have the stereochemical structure shown in formula (Ia) and (IIa)

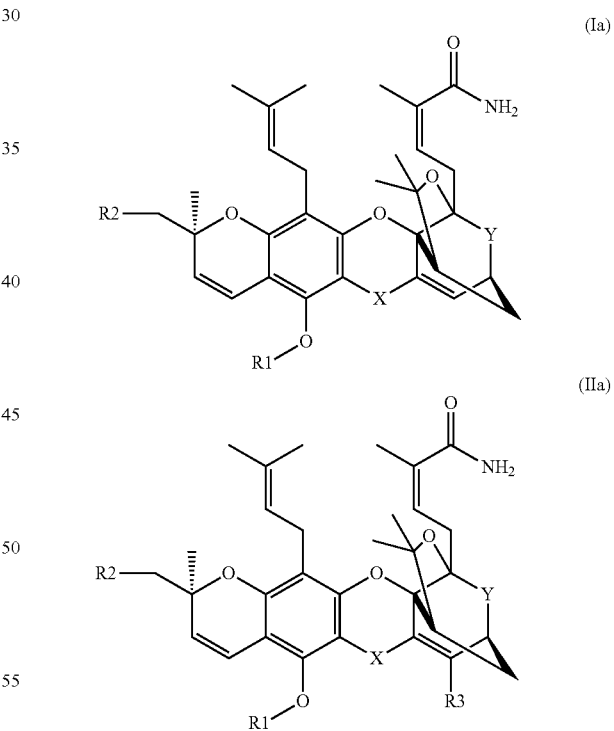

In the most preferred embodiment, the compound is defined by formula (I) or (Ia) and $R_1$ is hydrogen, $R_2$ is prenyl, X is carbonyl and Y is carbonyl. This compound characterized by formula (Ia) will be referred to as "gambogic acid amide".

The term "glioblastoma" or "glioblastoma multiforme" refers to a primary brain tumor involving glial cells. Glioblastoma is, preferably, diagnosed based on the histological presence of proliferative glial tumor cells, vascular proliferation and preferentially necrotic tissue areas (for further classification: Louis, D. N., Ohgaki, H., Wiestler, O.D., Cavenee, W. K., Burger, P. C., Jouvet, A., Scheithauer, B. W., and Kleihues, P. 2007. The 2007 WHO classification of tumours of the central nervous system. Acta Neuropathol 114:97-109.

The study underlying the present invention demonstrated that the compounds of the invention were equally effective against primary and recurrent glioblastoma of the same patient, glioblastoma with increased and decreased methylation of the promoter of the gene O6-Methylguanin-Methyltransferase (MGMT), glioblastoma with as well as without mutated p53; and glioblastoma with wildtype of nuclear factor of kappa light polypeptide gene enhancer in B-cells inhibitor (NFKBIA) as well as with heterozygous deletions of NFKBIA.

Therefore, the term "glioblastoma", preferably, refers to glioblastoma irrespective of the methylation status of the MGMT-promoter, glioblastoma with and without mutated p53, glioblastoma with or without alterations of the gene encoding NFKBIA, glioblastoma with and without alterations of the gene encoding epidermal growth factor receptor (EGFR), glioblastoma with and without alterations of the gene encoding platelet-derived growth factor receptor (PDGFRA), glioblastoma with and without alterations of the gene encoding isocitrate dehydrogenase 1 (IDHI) and glioblastoma with and without alterations of the gene encoding neurofibromatosis type 1 (NF1). Is to be understood the term "glioblastoma" also encompasses a glioblastoma characterized by any combination of at least two of the features set forth above.

The term "alterations" refers to mutations, deletions and the presence of additional copies of the gene in question. Mutations and deletions may be homo- or heterozygous. Moreover, the term "glioblastoma" refers to primary as well as recurrent disease.

In a preferred embodiment, the glioblastoma comprises cells with stem-like properties. Preferably a cell with stem like properties is defined by three features: (i) multipotency, (ii) the ability of self-renewal and (iii) tumorigenicity. Cells with the aforementioned features can preferably be detected by determining the expression status of at least one gene selected from the group consisting of CD133, ATP-binding cassette sub-family G member 2 (ABCG2), Aldehyde Dehydrogenase 1 (ALDH1A1), musashi homolog 1 (MSI-1), Nestin and sex determining region Y-box 2 (SOX-2). According to the present invention the most preferred marker is CD133.

In a particularly preferred embodiment of the invention, the glioblastoma comprises a proportion of cells with stem-like properties which is higher than the proportion typically found in a glioblastoma. The proportion of stem-like cells typically found in a glioblastoma is, preferably, defined by measuring the average proportion of said cells in a representative number of glioblastomas. Preferably, the average proportion is based on the determination of the proportion of stem-like cells in at least 20, at least 50 or at least 100 glioblastomas. Preferably, the glioblastomas used for the definition of the average proportion of stem-like cells are selected randomly.

Preferably, cells with stem-like properties are characterized by over-expression of at least one of the genes recited above as compared to a cell without stem-like properties. As the proportion of stem-like cells in a tumor is typically small (below 1%), it is also possible to use the expression of the gene in question in an arbitrarily chosen part of a tumor biopsy as basis for the comparison.

A preferred method for determining the expression status of the genes recited above in a cell or a group of cells is flow-cytometry. This method is well known to the person skilled in the art. It is well suited for the differentiation of populations of cells which differ with respect to the expression of at least one gene, preferably on the cell surface. Based on the results it is possible to determine a suitable threshold value which defines whether or not a certain gene is over-expressed in the cell or group of cells in question.

The validity of the determined threshold value can be tested by performing control experiments which demonstrate that the cells designated as "stem-like" according to flow-cytometry indeed possess the properties of (i) multipotentcy, (ii) ability of self-renewal and (iii) tumorigenicity. According to the present invention it is not required that each cell designated as "stem-like" possesses said ability while none of the cells not designated as "stem-like" possesses it. However, it is required that a statistically significant higher proportion of "stem-like" cells possesses said properties as compared to the population of cells not designated as "stem-like". This can be confirmed by well known statistical tests such as Student's t-test.

The term "over-expression", preferably, refers to an expression which is increased by a factor of at least 2, a factor of at least 3 or a factor of at least 4 as compared to a cell from the same tumor not having stem-like properties or as compared to the average expression of the gene in a part of the tumor. In a more preferred embodiment any expression of at least one of the genes recited above indicates that the cell or group of cells in question has stem-like properties.

In an embodiment of the present invention, the compounds outlined above are present as pharmaceutically acceptable salts. The term "pharmaceutically acceptable salt" refers to a salt of the compound of the present invention. Suitable pharmaceutically acceptable salts of the compound of the present invention include acid addition salts which may, for example, be formed by mixing a solution of the compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound of the invention carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include but are not limited to: acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/ diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of general formula (I)-(III). A prodrug is a pharmacologically active or inactive compound that is modified chemically through in vivo physiological action, such as hydrolysis, metabolism and the like, into a compound of this invention following administration of the prodrug to a patient. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme. The suitability and techniques involved in making and using prodrugs are well known by those skilled in the art. For a general discussion of prodrugs involving esters, see Svensson and Tunek, Drug Metabolism Reviews 16.5 (1988), and Bundgaard, Design of Prodrugs, Elsevier (1985). Examples of a masked acidic anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 0 039 051 (Sloan and Little, Apr. 11, 1981) discloses Mannich-base hydroxamic acid prodrugs, their preparation and use.

Compounds of the present invention and also the starting materials for their preparation according to the invention can be synthesized as shown herein, and, alternatively, by methods and standard procedures known to those skilled in the art, i.e. as described in the literature (for example in the standard works, such as Houben-Weyl, Methoden der organischen Chemie [Methods of Organic Chemistry], Georg-Thieme-Verlag, Stuttgart), under reaction conditions which are known to those skilled in the art and suitable for the said reactions.

If desired, the starting materials can also be formed in situ by not isolating them from the reaction mixture, but instead immediately converting them further into the compounds of the present invention. On the other hand, it is possible to carry out the reaction stepwise. It should be noted that the general procedures are shown as it relates to preparation of compounds having unspecified stereochemistry. However, such procedures are generally applicable to those compounds of a specific stereochemistry, e.g., where the stereochemistry at a sterogenic center is (S) or (R). In addition, the compounds having one stereochemistry (e.g., (R)) can often be utilized to produce those having opposite stereochemistry (i.e., (S)) using well-known methods, for example, by inversion.

Certain compounds of the present invention can exist in unsolvated forms as well as in solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds. The racemates, enantiomers, diastereomers, geometric isomers and individual isomers are all intended to be encompassed within the scope of the present invention. Accordingly, the compounds of this invention include mixtures of stereoisomers, especially mixtures of enantiomers, as well as purified stereoisomers, especially purified enantiomers, or stereoisomerically enriched mixtures, especially enantiomerically enriched mixtures. Also included within the scope of the invention are the individual isomers of the compounds represented by formulas (I) to (III) below as well as any wholly or partially equilibrated mixtures thereof. The present invention also covers the individual isomers of the compounds represented by the formulas below as mixtures with isomers thereof in which one or more chiral centers are inverted. Also, it is understood that all tautomers and mixtures of tautomers of the compounds of formulas (I) to (III) are included within the scope of the compounds of formulas (I) to (III) and preferably the formulas and subformulas corresponding thereto.

Racemates obtained can be resolved into the isomers mechanically or chemically by methods known per se. Diastereomers are preferably formed from the racemic mixture by reaction with an optically active resolving agent.

Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as -camphorsulfonic acid. Also advantageous is enantiomer resolution with the aid of a column filled with an optically active resolving agent (for example dinitrobenzoylphenylglycine); an example of a suitable eluent is a hexane/isopropanol/acetonitrile mixture.

The diastereomer resolution can also be carried out by standard purification processes, such as, for example, chromatography or fractional crystallization.

It is also possible to obtain optically active compounds of formulas (I) to (III) by the methods described above by using starting materials which are already optically active.

In a further aspect the present invention relates to a pharmaceutical composition comprising a compound according to formula I, Ia, II, IIa or III, wherein X, Y, $R_1$, $R_2$ and $R_3$ have the meaning and preferred meanings set out above, for the treatment of glioblastoma.

A "pharmaceutical composition" as referred to in the present application comprises at least one compound of the present invention and at least one pharmaceutically acceptable carrier.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 80%, more preferably from 20% to 70% of the active compound or active compounds. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. Liquid forms are particularly preferred for topical applications to the eye. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In a preferred embodiment of the present invention, the pharmaceutical composition additionally comprises at least one further cytostatic or cytotoxic compound. Said additional compound is selected from the group consisting of temozolomide Daunorubicine, Gambogic acid amide, Gambogic acid, Thimerosal, Mitoxanthrone hydrochloride, Phenylmercuric acetate, Dactinomycin, Pristimerin, Epirubicin hydrochloride, Vincristine sulfate, Emetine, Paclitaxel, 10-Hydroxycamptothecin, Doxorubicine, Colchicine, Camptothecin, Teniposide, Vinblastine sulfate, Mitomycin C, Floxuridine, Ouabain, Ancitabine hydrochloride, Quinacrine hydrochloride, Niclosamide, Amsacrine, Thioguanine, Rotenone, Aklavine hydrochloride, Cytarabine, Methotraxate, and Picropodophyllotoxin.

Further preferred additional cytostatic or cytotoxic compounds include anti-estrogens such as faslodex, tamoxifen or raloxifen; any inhibitors of topoisomerase I or II, such as camptothecin (topo I) or etoposide (topo II); any compound that acts through inhibiting aromatase activity, such as anastrozole or letrozole; any preparation that interferes with HER2 signalling such as herceptin; any compound that interchelates DNA, such as doxorubicin. Particularly preferred cytostatic or cytotoxic drugs, which can be combined with the compounds of the present invention are alkylating substances, anti-metabolites, antibiotics, epothilones, nuclear receptor agonists and antagonists, anti-androgenes, anti-estrogens, platinum compounds, hormones and antihormones, interferons and inhibitors of cell cycle-dependent protein kinases (CDKs), inhibitors of cyclooxygenases and/or lipoxygenases, biogeneic fatty acids and fatty acid derivatives, including prostanoids and leukotrienes, inhibitors of protein kinases, inhibitors of protein phosphatases, inhibitors of lipid kinases, platinum coordination complexes, ethyleneimenes, methylmelamines, trazines, vinca alkaloids, pyrimidine analogs, purine analogs, alkylsulfonates, folic acid analogs, anthracendiones, substituted urea, methylhydrazin derivatives, in particular acediasulfone, aclarubicine, ambazone, aminoglutethimide, L-asparaginase, azathioprine, bleomycin, busulfan, calcium folinate, carboplatin, carpecitabine, carmustine, celecoxib, chlorambucil, cis-platin, cladribine, cyclophosphamide, cytarabine, dacarbazine, dactinomycin dapsone, daunorubicin, dibrompropamidine, diethylstilbestrole, docetaxel, doxorubicin, enediynes, epirubicin, epothilone B, epothilone D, estramucin phosphate, estrogen, ethinylestradiole, etoposide, flavopiridol, floxuridine, fludarabine, fluorouracil, fluoxymesterone, flutamide fosfestrol, furazolidone, gemcitabine, gonadotropin releasing hormone analog, hexamethylmelamine, hydroxycarbamide, hydroxymethylnitro furantoin, hydroxyprogesteronecaproat, hydroxyurea, idarubicin, idoxuridine, ifosfamide, interferon γ, irinotecan, leuprolide, lomustine, lurtotecan, mafenide sulfate olamide, mechlorethamine, medroxyprogesterone acetate, megastrolacetate, melphalan, mepacrine, mercaptopurine, methotrexate, metronidazole, mitomycin C, mitopodozide, mitotane, mitoxantrone, mithramycin, nalidixic acid, nifuratel, nifuroxazide, nifuralazine, nifurtimox, nimustine, ninorazole, nitrofurantoin, nitrogen mustards, oleomucin, oxolinic acid, pentamidine, pentostatin, phenazopyridine, phthalylsulfathiazole, pipobroman, prednimustine, prednisone, preussin, procarbazine, pyrimethamine, raltitrexed, rapamycin, rofecoxib, rosiglitazone, salazosulfapyridine, scriflavinium chloride, semustine streptozocine, sulfacarbamide, sulfacetamide, sulfachlopyridazine, sulfadiazine, sulfadicramide, sulfadimethoxine, sulfaethidole, sulfafurazole, sulfaguanidine, sulfaguanole, sulfamethizole, sulfamethoxazole, co-trimoxazole, sulfamethoxydiazine, sulfamethoxypyridazine, sulfamoxole, sulfanilamide, sulfaperin, sulfaphenazole, sulfathiazole, sulfisomidine, staurosporin, tamoxifen, taxol, teniposide, tertiposide, testolactone, testosteronpropionate, thioguanine, thiotepa, timidazole, topotecan, triaziquone, treosulfan, trimethoprim, trofosfamide, UCN-01, vinblastine, vincristine, vindesine, vinblastine, vinorelbine, and zorubicin, or their respective derivatives or analogs thereof.

In a particularly preferred embodiment of the present invention the additional cytostatic or cytotoxic compound is temozolomide.

Salts/Esters

The compounds within the compositions or compounds usable according to the present invention can be present as salts or esters, in particular pharmaceutically acceptable salts or esters. Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Isotopes

The compounds of the present invention may also contain unnatural proportions of atomic isotopes at one or more of the atoms that constitute such compounds. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{3}H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

All isotopic variations of the compounds and compositions of the present invention, whether radioactive or not, are intended to be encompassed within the scope of the present invention.

Solvates

The present invention also includes solvate forms of the compounds within the compositions or compounds according to any of general formulas (I) through (III) usable according to the present invention. The terms used in the claims encompass these forms.

Polymorphs

The invention furthermore relates to compounds within the compositions of the present invention or compounds according to formula (I) usable according to the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

A compound according to the invention can be administered by various well known routes, including oral, rectal, intragastrical, intracranial and parenteral administration, e.g. intravenous, intramuscular, intranasal, intradermal, subcutaneous, and similar administration routes. Parenteral administration and particular intravenous administration, preferably by depot injection, is preferred. Depending on the route of administration different pharmaceutical formulations are required and some of those may require that protective coatings are applied to the drug formulation to prevent degradation of a compound of the invention in, for example, the digestive tract.

Thus, preferably, a compound of the invention is formulated as a syrup, an infusion or injection solution, a tablet, a capsule, a capslet, lozenge, a liposome, a suppository, a plaster, a band-aid, a retard capsule, a powder, or a slow release formulation. Preferably the diluent is water, a buffer, a buffered salt solution or a salt solution and the carrier preferably is selected from the group consisting of cocoa butter and vitebesole.

Particular preferred pharmaceutical forms for the administration of a compound of the invention are forms suitable for injectionable use and include sterile aqueous solutions or dispersions and sterile powders for the extemporaneous preparation of sterile injectable solutions or dispersion. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. A compound of the invention can also be formulated into liposomes, in particular for parenteral administration. Liposomes provide the advantage of increased half life in the circulation, if compared to the free drug and a prolonged more even release of the enclosed drug.

Sterilization of infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride may be incorporated in infusion or injection solutions.

Production of sterile injectable solutions containing one or several of the compounds of the invention is accomplished by incorporating the respective compound in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Besides the preferred excipients mentioned already above, also the following excipients can be chosen, without limitation, to be used with the various pharmaceutical forms of a compound of the invention:

a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;
b) lubricants such as magnesium stearate, talc, calcium stearate, zinc stearate, stearic acid, hydrogenated vegetable oil, leucine, glycerides and sodium stearyl fumarates,
c) disintegrants such as starches, croscaramellose, sodium methyl cellulose, agar, bentonite, alginic acid, carboxymethyl cellulose, polyvinyl pyrrolidone and the like.

Other suitable excipients can be found in the Handbook of Pharmaceutical Excipients, published by the American Pharmaceutical Association, which is herein incorporated by reference.

It is to be understood that depending on the severity of the disorder and the particular type which is treatable with one of the compounds of the invention, as well as on the respective patient to be treated, e.g. the general health status of the patient, etc., different doses of the respective compound are required to elicit a therapeutic or prophylactic effect. The determination of the appropriate dose lies within the discretion of the attending physician.

As is known in the art, the pharmaceutically effective amount of a given composition will also depend on the administration route. In general the required amount will be higher, if the administration is through the gastrointestinal tract; e.g. by suppository, rectal, or by an intragastric probe, and lower if the route of administration is parenteral, e.g. intravenous.

Within the meaning of this invention, a combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week. This invention also envisions the quaternization of any basic nitrogen-containing groups of the compounds disclosed herein. Water or oil-soluble or dispersible products may be obtained by such quaternization.

A further embodiment of the present invention relates to a method for determining if treatment with a compound according to formula I, II or III, wherein X, Y, $R_1$, $R_2$ and $R_3$ have the meaning set out above is suitable for a patient comprising the steps of a) determining the expression level of a gene selected from the group consisting of CD133, ATP-binding cassette sub-family G member 2 (ABCG2), Aldehyde Dehydrogenase 1 (ALDH1A1), musashi homolog 1 (MSI-1), Nestin and sex determining region Y-box 2 (SOX-2) in a sample of tumor tissue or tumor cells of the patient;
b) comparing the expression level determined in step a) with a reference value; and
c) determining whether treatment with a compound according to formula I, II or III is suitable for a patient based on the result of the comparison of step b), wherein over-expression indicates that said treatment is suitable for the patient.

Preferably, the method of the invention is performed in vitro. The patient, preferably, suffers from glioblastoma.

Methods for determining the expression level of a gene are well known to the person skilled in the art. Gene expression can be determined by measuring the amount of mRNA-transcripts of the gene in question and it can also be determined by measuring the amount of the protein encoded by the gene. Preferred methods based on the measurement of the amount of mRNA-transcripts generated include quantitative real-time PCR and hybridization based on techniques such as microarrays. Preferred methods for the measurement of the amount of a specific protein include immunological methods such as the enzyme-linked immunosorbent assay (ELISA). Especially preferred is the use of methods which allow the determination of gene expression on the level of single cells because in typical cases only few cells in a tumor are stem-like cells. Methods which determine gene expression in a large amount of cells generate average values which may cover the deviating values of small subpopulations of stem-like cells.

Therefore the hybridization of labelled probes to the transcript or detection of the protein encoded by the gene in question with an antibody and the subsequent determination of the strength of the signal generated by single cells is one preferred method for the determination of gene-expression. For this purpose flow cytometry of cells labelled with a suitable antibody is preferred.

Methods for defining and validating suitable threshold values which define over-expression are described above. The presence of cells which over-express at least one of the genes recited above indicates that treatment with a compound according to formula I, II or III is suitable for the patient.

In a preferred embodiment of the present invention, the proportion of tumor cells overexpressing at least one of the above-mentioned genes is determined. If the proportion of said cells in the individual tumor is higher than the average proportion found in a representative number of tumors, treatment with a compound according to formula I, II or III is particularly suitable for the patient.

Further preferred embodiments of the present invention are given below in items 1 to 11.

1. A method for inhibiting human patient-specific glioblastoma cells, said method comprising: contacting said glioblastoma cells with at least one compound selected from the group consisting of: cytotoxic and/or cytostatic compounds, wherein said compound exhibits an inhibitory metabolic activity effect in vitro greater than temozolomide on said glioblastoma cells.

2. The method according to item 1, wherein said contacting of said glioblastoma cells with said cytotoxic and/or cytostatic compound induces apoptosis in said glioblastoma cells, inhibits NF-kB signaling, and induces the expression of HSp70.

3. The method according to item 1, wherein said cytotoxic and/or cytostatic compounds are at least one selected from the group consisting of: daunorubicin, gambogic acid amide, gambogic acid, thimerosal, mitoxantrone hydrochloride, phenylmercuric acetate, dactinomycin, pristimerin, epirubicin hydrochloride, vincristine sulfate, emetine, paclitaxel, 10-hydroxycamptothecin, doxorubicin, colchicine, camptothecin, teniposide, vinblastine sulfate, mitomycin C, floxuridine, ouabain, ancitabine hydrochloride, quinacrine hydrochloride, niclosamide, amsacrine, thioguanine, rotenone, aklavine hydrochloride, cytarabine, methotrexate, and picropodophyllotoxin.

4. The method according to item 3, wherein said cytotoxic and/or cytostatic compounds are at least one selected from the group consisting of: gambogic acid amide, gambogic acid, pristimerin, epirubicin hydrochloride, emetine, ouabain, ancitabine hydrochloride, quinacrine hydrochloride, niclosamide, amsacrine, aklavine hydrochloride, and picropodophyllotoxin.

5. The method according to item 4, wherein said cytotoxic and/or cytostatic compound is pristimerin, wherein said pristimerin is added in a concentration in the range between about 0.1 to about 10 µM in particular between about 0.9 to about 1.3 µM.

6. The method according to item 1, wherein said glioblastoma cells comprise a subset of stem-like cells.

7. The method according to item 1, wherein said contacting of said glioblastoma cells with said cytotoxic and/or cytostatic compound delays cell growth of said glioblastoma cells for up to 10 days after said contacting.

8. A glioblastoma growth-inhibiting compound that is at least one compound selected from the group consisting of: cytotoxic and cytostatic compounds, wherein said compound exhibits an inhibitory metabolic activity effect in vitro greater than temozolomide for glioblastoma patients.

9. The compound according to item 8, wherein said compound induces apoptosis in said glioblastoma cells, inhibits NF-kB signaling, and induces the expression of HSp70.

10. The compound according item 8, wherein said cytotoxic and/or cytostatic compounds are at least one selected from the group consisting of: daunorubicin, gambogic acid amide, gambogic acid, thimerosal, mitoxantrone hydrochloride, phenylmercuric acetate, dactinomycin, pristimerin, epirubicin hydrochloride, vincristine sulfate, emetine, paclitaxel, 10-hydroxycamptothecin, doxorubicin, colchicine, camptothecin, teniposide, vinblastine sulfate, mitomycin C, floxuridine, ouabain, ancitabine hydrochloride, quinacrine hydrochloride, niclosamide, amsacrine, thioguanine, rotenone, aklavine hydrochloride, cytarabine, methotrexate, and picropodophyllotoxin.

11. The compound according to item 10, wherein said cytotoxic and/or cytostatic compounds are at least one selected from the group consisting of: gambogic acid amide, gambogic acid, pristimerin, epirubicin hydrochloride, emetine, ouabain, ancitabine hydrochloride, quinacrine hydrochloride, niclosamide, amsacrine, aklavine hydrochloride, and picropodophyllotoxin.

The following examples and figures are merely illustrative of the present invention and should not be construed to limit the scope of the invention, as indicated by the appended claims, in any way.

DESCRIPTION OF THE FIGURES

FIG. 14: Pharmacodynamic analysis. (A) Gambogic acid and Gambogic acid amide inhibit the metabolic activity of pGBMs effectively and to a comparable degree. (B) Data demonstrate, however, that the induction of Gambogic acid amide's inhibitory activity occurs at an earlier time point. Graphs indicate relative metabolic activity of pGBMs (#'s indicated) at day 1 (rhombus), 2 (square), or 5 (triangle) following compound exposure (concentration indicated). Data as mean±SD of triplicates.

FIG. 16: Cell cycle analysis. pGBMs (#'s indicated) were exposed to DMSO-control or compounds at the respective IMC50- and 1 µM-concentrations for 5 days. Cytometric analysis was conducted applying standard protocols. PI, propidium iodide; n.d., not determined (due to massive cell loss at the respective compound concentration).

FIG. 17: Neurosphere assay. The assay was used to estimate potential alterations to the pool of self-renewing and multipotent cells within pGBMs (n=3: #'s 046; 106; 138; triplicate analysis for all samples). The frequency of primary (1°), secondary (2°), and tertiary) (3° neurospheres was determined following a single pre-treatment with compounds at the indicated concentrations. (A) Gambogic acid pre-treatment did not alter the frequency of self-renewing cells. (B) By contrast, Gambogic acid amide pre-treatment led to a considerable decrease of self-renewing cells in the pGBMs investigated.

FIG. 18: Gambogig acid amide decreases the tumor-initiating potential of pGBMs. pGBMs (#046) were treated with IMC50 concentrations of the respective compounds for 5 days in vitro. 106 surviving vital cells were subsequently collected and injected into the striatum of adult immunocompromised mice (n=5 for each experiment). (A) Kaplan-Meier curves show no significant survival advantage upon injection of pGBMs pre-treated with gambogic acid (dotted) vs. DMSO controls (solid). (B) By contrast, gambogic acid amide-pretreated (dotted) pGBMs appeared significantly less tumorigenic compared to the respective controls (DMSO; solid).

FIG. 19: Preferred targeting of $CD133^+$ GBM cells by Gambogig acid amide. (A) FACS-based identification and sorting of $CD133^+$ subpopulations from pGBMs (#106, top; #058, bottom). Note the respective frequency of $CD133^+$ cells is indicated within the panel). (B) Relative metabolic activity and cell confluency of CD133-positive vs. CD133-negative pGBM cells determined at 5 days after single exposure of Gambogic acid (IMC50, top) and Gambogic acid amide (IMC50, bottom). Note the selective sensitivity of $CD133^+$ cells in response to application of Gambogic acid amide.

EXAMPLES

Example 1

Tissue Samples

Figure 1:
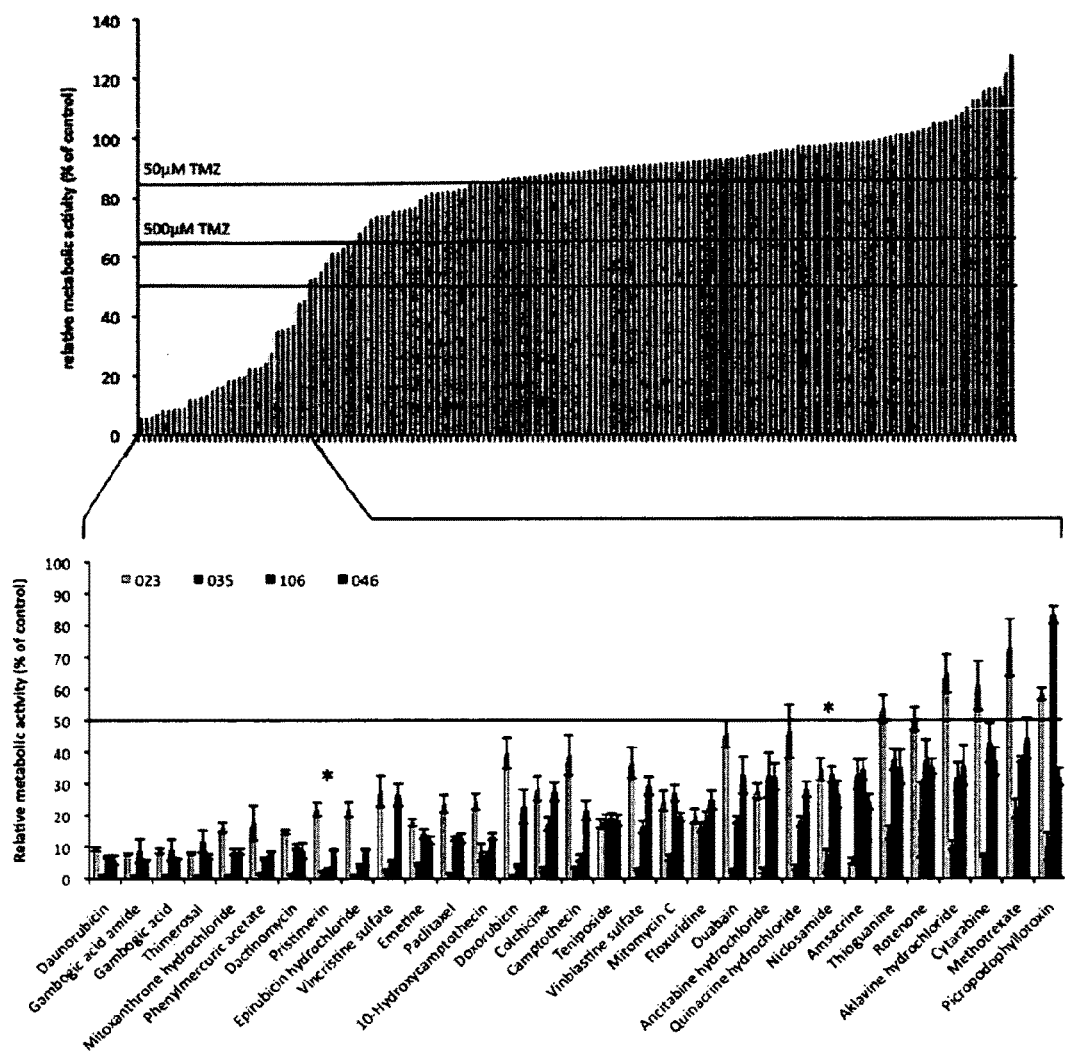
FIG. 1: (top) Rank-ordered diagram of the 160 compounds (x-axis) showing their effects on the metabolic activity 5 days after single dose application (1 µM each) (mean data from four patient-specific. GBM primary cultures relative to DMSO-treated cells). Based on the AlamarBlue® assay, we identified 31 "hit" compounds that reduced the relative metabolic activity to <50%. As a reference, cells were treated with 50 µM (orange line) and 500 µM temozolomide (TMZ; blue line). (inset) Detailed data presentation of the 31 hit compounds. Error bars represent the standard deviation of triplicate assay results.

Tumor tissue was obtained from GBM surgery at the Department of Neurosurgery, University of Bonn Medical Centre. The study was approved by the local Ethics committee; all patients provided informed consent. Histology of all biopsy samples was performed based on the current classification of the World Health Organization (Louis et al., ActaNPT 2007) and con-firmed by two independent neuropathologists at the Department of Neuropathology, University of Bonn Medical Centre (the National Reference Center of Neuropathology).

TABLE 1

| Case ID | Diagnosis | Sex | Age | Neurosphere Frequency | Multipotent Neurospheres? | Tumor formation in xenograft model? |
|---|---|---|---|---|---|---|
| #023 | New GBM | f | 89 | 0.28/0.32/0.39 | Yes, neurons, glia, oligodendrocytes | No |
| #035 | New GBM | f | 75 | 0.1/0.1/0.18 | Yes, neurons and glia | Yes, diffusely invasive glioma at 300 dptx |

TABLE 1-continued

| Case ID | Diagnosis | Sex | Age | Neurosphere Frequency | Multipotent Neurospheres? | Tumor formation in xenograft model? |
|---|---|---|---|---|---|---|
| #046 | New GBM | m | 76 | 0.5/0.76/1.1 | Yes, neurons and glia | Yes, patient-specific GBM at 60-90 dptx |
| #106 | New GBM | f | 68 | 0.98/0.960.89 | Under investigation | Yes |

Table 1: Patient data and characterization of the four primary GBm cultures used for compound screening. Neurosphere frequency was determined in the NSA for 1°/2°/3° neurospheres, respectively. Multipotency was determined by plating of 2° and 3° neurospheres, followed by a 21 day differentiation process, and immuocytochemistry was conducted with markers characteristically expressed in neurons (beta III tubulin), astrocytes (GFAP) and oligodendrocytes (CNPase).
Age: Patient age at surgery;
dpts: days psot transplantation;
Sex: m = male;
f = female.

Tissue Handling and Primary Culture

Biopsy samples were received 30 to 60 minutes after resection and the tissue was subsequently dissected under sterile conditions into three representative fractions. One fraction was fixed with 4% paraformaldehyde (PFA) for histological analysis, the second fraction underwent snap freezing in liquid nitrogen for molecular analysis, and the third fraction was gently titurated to prepare a single cell suspension using a 0.25% buffered trypsin solution and fire polished Pasteur pipettes. The single cell suspension was plated into adhesive culture conditions for cell expansion in proliferative media (PROL; composition according to Lee et al., 2006) into 6 cm laminin/poly-L-ornithine coated plastic dishes. 20 ng/ml EGF/bFGF was provided upon plating, and 10 ng/ml EGF/bFGF was then added every other day thereafter. Adherent cells were propagated by serial passaging in ratios of 1:2 or 1:3 every 4-7 days.

Neurosphere Assay

Based on previous investigations (Scheffler et al., 2005), a single cell suspension of $1 \times 10^4$ cells/cm$^2$ was diluted in 1% methylcellulose-containing PROL media provided with 20 ng/ml EGF/bFGF, and inoculated into nonadhesive culture dishes. 10 ng/ml EGF/bFGF was then added every other day. Neurospheres were quantified at 21 days in culture, triturated to a single cell suspension, which was used for plating under identical conditions and analysis of the formation of secondary or higher degree neurospheres. For analysis of multipotency, a representative fraction of 3° neurospheres were used. Neurospheres were plated onto laminin/poly-L-ornithine coated glass coverslips and, after attachment, provided with PROL media devoid of mitogens to allow differentiation for 2-3 weeks in culture before PFA-fixation and immunofluorescence analysis.

Fluorescence Analysis

Immunofluorescence analysis of cultured cells was performed on 4% PFA-fixed samples according to standard protocols (Scheffler et al., 2005; Goetz et al., 2006) using antibodies against pIII tubulin (Promega, Mannheim, Germany; monoclonal mouse, 1:1000), CNPase (Millipore, Schwalbach, Germany; monoclonal mouse, 1:300) and GFAP (DAKO, Hamburg, Germany; polyclonal rabbit, 1:600). Cell nuclei were visualized by labeling with DAPI (Sigma).

Western Blot Analysis

Cells were incubated with compounds for 24 h with the concentrations indicated. Cell extracts were prepared and processed as described (Wiechen et al., 2001). Western blot membranes were incubated overnight at 4° C. with a Cyclin-D1 (1:1000; BD Pharmingen, Heidelberg, Germany), an Hsp-70 (1:1000), a cleaved-Notch 1 (1:1000), a phospho-S6 protein (1:1000), a pIkB (1:1000), a phospho-catenin (Ser33/37/Thr41) (1:1000), a phospho-IKBa (Ser32) (1:1000) and a p85/p55-PI3K antibody (1:1000; all Cell signaling, Frankfurt am Main, Germany). After extensive washing, peroxidase-coupled secondary antibodies (Santa-Cruz, Heidelberg, Germany) were added for 1 h. After washing, blots were developed using the ECL system (AmershamPharmacia, Buckingshamshire, UK). To confirm equal loading, blots were reprobed with a p-actin antibody (Sigma, Deisenhofen, Germany).

Proliferation Kinetics

Five days after treatment in 6 cm dishes, 47,000 vital cells were plated into 3.5 cm laminin/poly-L-ornithine coated plastic dishes. 20 ng/ml EGF/bFGF were provided upon plating, and 10 ng/ml EGF/bFGF were added every other day thereafter. Four-to-six days later, adherent cells were trypsinized, harvested, counted, and plated at a density of $4.7 \times 10^4$ cells. This procedure was repeated for 4-5 passages. Mean values are presented with standard error.

Flow Cytometry

Cells were collected four days after compound treatment in 6 cm dishes. $1 \times 10^5$ cells were sedimented by centrifugation, resuspended in 1000 AnnexinV buffer (BD Bioscience, Heidelberg, Germany) and incubated with 5 µl Annexin V-FITC (BD Bioscience, Heidelberg, Germany) for 1 h at RT. To distinguish between living and dead cells, labeling with 1.2 µg/ml bisbenzimide H33258 (Invitrogen, Karlsruhe, Germany) was used. Expression was determined using standard conditions in a LSRII equipped with FACSDiva Software (BD Bioscience, Heidelberg, Germany). For each measurement, 20.000 cells were counted. Annexin V positive cells, Annexin V and H33258 positive cells and H33258 positive cells were termed avital cells.

Drug Screening

Various compounds obtained from Microsource Discovery Systems, Inc., Gayordsville, Conn., USA were screened. Before screening, cell number was titrated for each cell line separately to ensure that cell proliferation remained in a linear-exponential phase throughout the experiment. 24 hours after seeding $2-3 \times 10^3$ cells/well into laminin/poly-L-ornithine coated 96-well plates, primary cultures were treated with 2 nM, 1 µM or 10 µM of each compound (stock solution 10 mM in DMSO). As a reference we treated cells with 50 µM and 500 µM temozolomide (TMZ, SigmaAldrich, Taufkirchen, Germany; stock solution of 100 mM in DMSO). Control cells were treated with 0.5-0.01% DMSO. Six days after application, cell viability was determined using the AlamarBlue® assay according to the manufacturers recommendations (Invitrogen, Karlsruhe, Germany). Fluorescence was measured using an Infinite200 microplate reader (Tecan, Crailsheim, Germany) at Xex=540 nm and Xem=590 nm. Experiments were performed in triplicates for each sample.

For pharmacodynamic analyses of pristimerin and niclosamide $5 \times 10^4$ cells were plated in 12 well plates 24 h before they were treated with concentrations indicated. 5 days after the treatment, cell viability was monitored by the AlamarBlue® assay. Experiments were performed in triplicates. The $ICM_{50}$ is the concentration of agent that reduced the metabolic activity by 50% under the experimental conditions.

For further experiments primary GBM cells were plated at 40-50% confluence on laminin/poly-L-ornithine coated 6 cm dishes. Cells were treated with pristimerin and niclosamide in concentrations indicated. Control cells were treated with 0.1% DMSO.

Results and Discussion

To identify cytotoxic and cytostatic compounds, we conducted in vitro drug-screening assays in four different patient-specific primary GBM cultures (see Table 1 for basic characterization of research specimens).

The compound library was screened at three different concentrations (10 µM, 1 µM, 2 nM). The relative metabolic activity was determined after a 5-day incubation with compounds. The (1 µM)-data set is depicted in FIG. 1. At this concentration, 31 compounds qualified as hits, because they decreased the relative metabolic activity to less than 50% of the DMSO-treated controls (FIG. 1 top; red bars). For reference, we applied 50 µM (reported plasma peak concentration) and 500 µM of temozolomide (TMZ, as described in Beier et al., 2008), the current standard chemotherapeutic GBM drug to our cells. The application of 50 µM TMZ resulted in a 17% (orange line) reduction, while 500 µM TMZ reduced the relative metabolic activity of our four patient-specific primary cells to a level of 63% (mean data, blue line; FIG. 1 top). Thus, at concentrations of 1 µM, 39 resp. 61 of the screened compounds yielded stronger metabolic reductions in the activity of our patient specific GBM cells than TMZ at concentrations of 500 resp. 50 µM. However, "hits" in the setting of a primary screening were defined as a reduction of the relative metabolic activity under the level of 50% of DMSO-treated control cells. 31 of the screened compounds collection fulfilled this definition based on analysis of mean data derived from our four patient-specific GBM primary cells (FIG. 1). However, the degree of metabolic inhibition varied between the individual research specimens investigated. Only 26 compounds of the 31 "hits" reduced the metabolic activity in every patient-specific case to more than 50% (FIG. 1, bottom).

Figure 2:
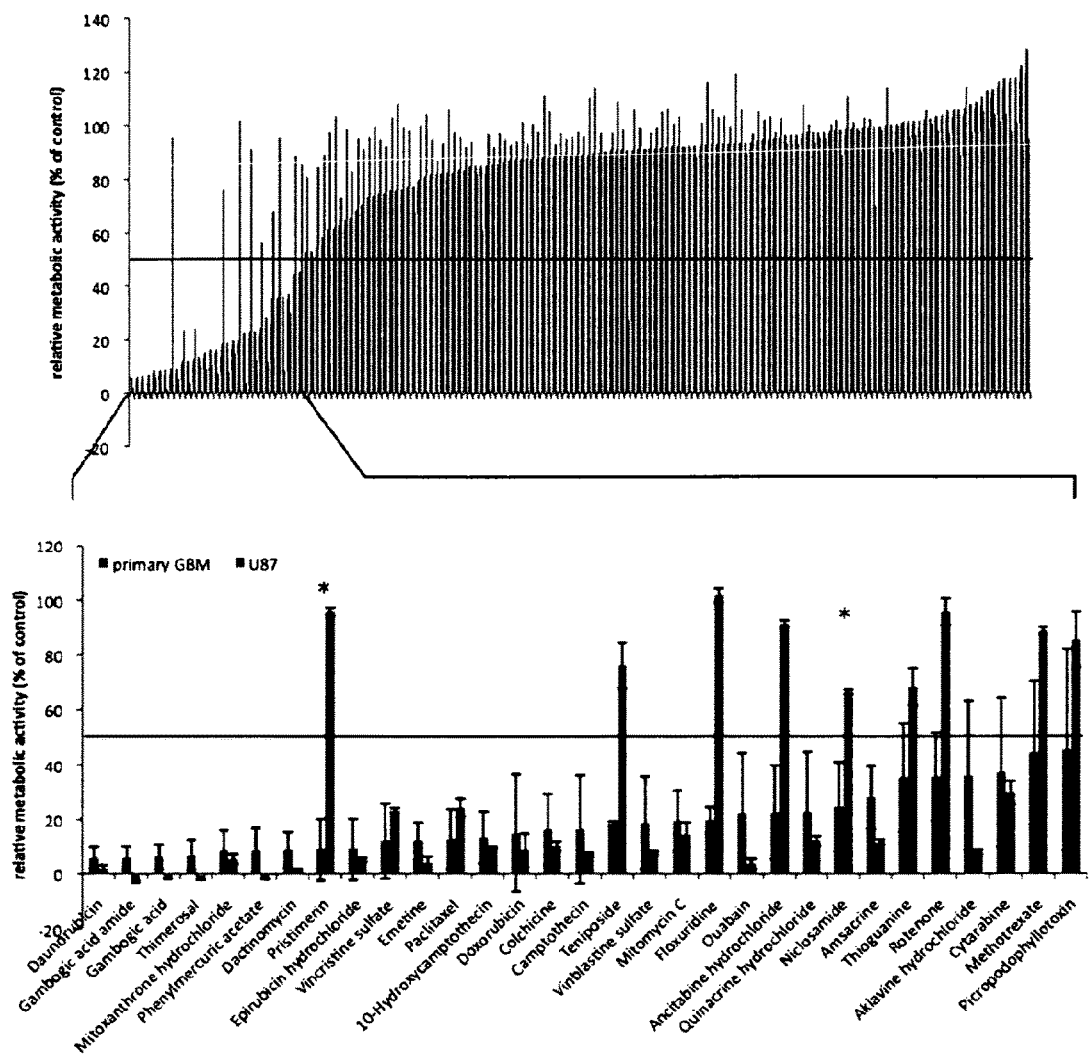
FIG. 2: (top) Comparative plot of the mean relative metabolic activities of our four patient-specific GBM samples and the U87 glioma celline in response to the 160 Killer•Plate® compounds. (inset) Detailed data on the 31 patient-specific "hit" compounds (bars on the left) in comparison to results obtained from analysis of the U87 glioma cell line (bars on the right). Error bars represent the standard deviation of triplicate assay results.

For comparison with our four patient-specific primary GBM cell specimens, we used the commercially available glioma cell line U87 that is frequently investigated in drug discovery settings (FIG. 2). Intriguingly, 9 of the patient-specific "hit" compounds (i.e. Pristimerin, Teniposide, Floxuridine, Ancitabine hydrochloride, Niclosamide, Thioguanine, Rotenone, Methotrexate, Picropodophyllotoxin) did not result in a >50% reduction of the relative metabolic activity of U87 (FIG. 2, bottom). In contrast, only one compound (Physicion) showed a significant influence on the U87's metabolic activity without affecting the primary GBM cells.

Figure 3:
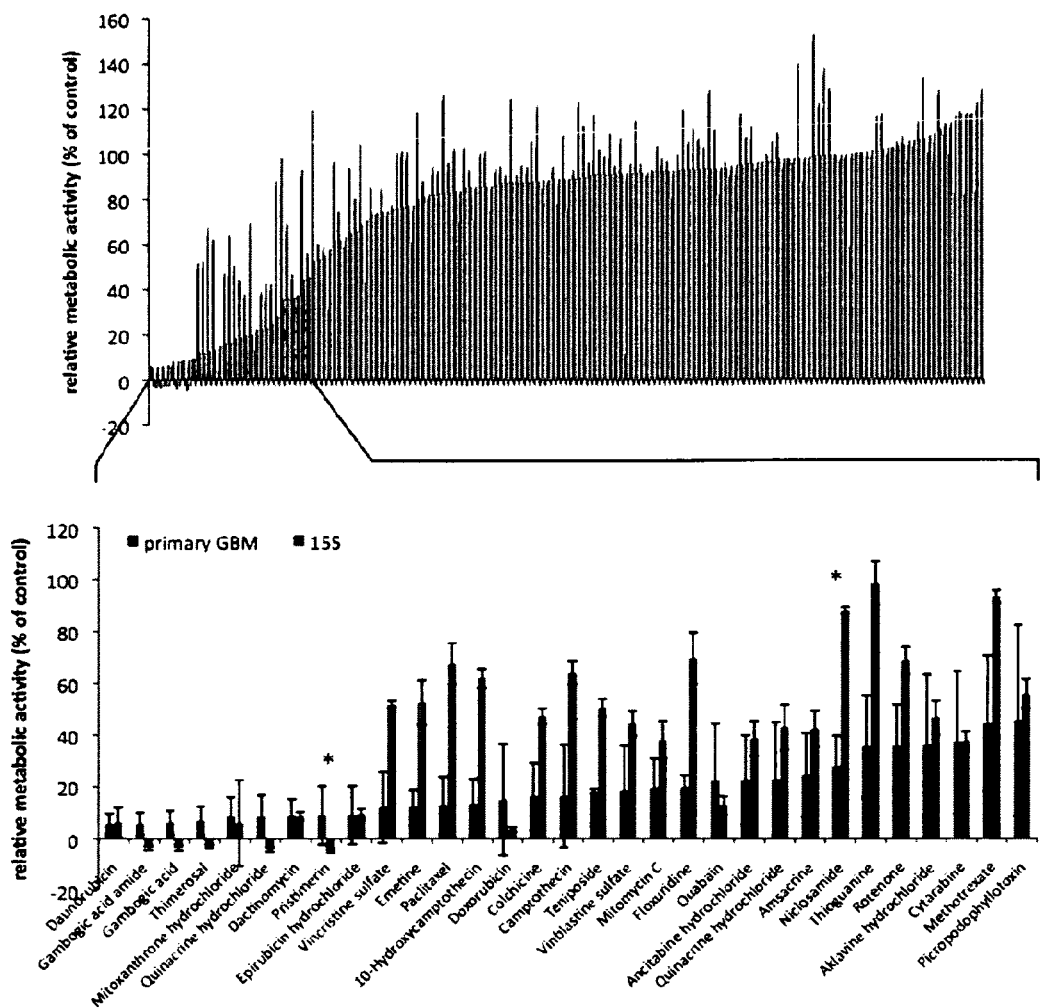
FIG. 3: (top) Comparative plot of the mean relative metabolic activities of four patient-specific GBM samples and the #155 cells in response to the 160 compounds. (inset) Detailed data on the 31 "hit" compounds. Mean relative metabolic activity in dark grey bars for the GBM primary cells and light grey bars for•the #155 cells. Error bars represent the standard deviation of triplicate assay results.

As an alternative control, primary cells were evaluated, which were obtained from a patient suffering from pharmacoresistent epilepsy (patient #155). Like the U87 cell line 155 cells showed a generally more resistant phenotype when exposed to the 31 "hit" compounds (FIG. 3). 11 of these compounds (i.e. 5 vincristine sulfate, emetine, paclitaxel, 10-Hydroxycamptothecin, camptothecin, teniposide, floxuridine, niclosamide, thioguanine, rotenone, methotrexate and picropodophyllotoxin) showed very little effect on the metabolic activity of the #155 cells (FIG. 3, bottom). 4 compounds (i.e. cytochalasin D, phorbol myristate acetate, Cantharidin, 2,3-dichloro-5,8-dihydroxynapthoquinone) diminished the metabolic activity of the #155 cells significantly but had no significant effect on the GBM primary cell (FIG. 3, top).

Several compounds among the 31 "hits" were excluded from further validation that (i) are/have been used in clinical applications for glioma therapy, i.e. daunorubicin, mitoxanthrone hydrochloride, vincristine sulfate, paclitaxel, 10-hydroxycamptothecin, doxorubicin, teniposide, vinblastine sulfate, floxuridine, thioguanine, and methotrexate; (ii) are/have been investigated in clinical trials for glioma, i.e. dactinomycin, 10-hydroxycamptothecin, mitomycin C, and cytarabine; or (iii) have shown significant toxicity in humans or animals, i.e. thimerosal, phenylmercuric acetate, colchicine, camptothecin and rotenone.

12 candidate compounds remained for further validation experiments (i.e. gambogic acid amide, gambogic acid, pristimerin, epirubicin hydrochloride, emetine, ouabain, ancitabine hydrochloride, quinacrine hydrochloride, niclosamide, amsacrine, aklavine hydrochloride, picropodophyllotox-in). All of these represent new potential candidates for GBM chemotherapy settings.

Pristimerin Validation Experiments

Figure 4:
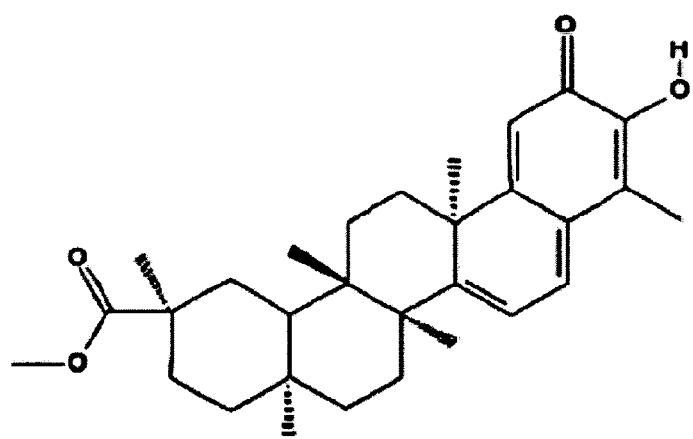
FIG. 4: Chemical structure of (a) pristimerin.

Pristimerin is a naturally occurring triterpenoid (FIG. 4) that can be found in Celastraceae and Hippocrateaceae families (Buffa Filho et al., 2002; Chenag et al., 2003; Niampoka et al., 2005). It can induce anti-inflammatory, anti-oxidant, anti-malarial and insecticidal processes (Sassa et al., 1994, Dirsch et al., 1997; Figueiredo et al., 1998; Avilla et al., 2000; Luo et al., 2005). In a dose-dependant manner, triterpenoids can induce cytoprotective, tumor-differentiating, proliferation-arresting, and apoptotic effects (Suh et al., 1999; Suh et al., 2003; Ji et al., 2006). Pristimerin can block NF-κB signaling in myeloma (Tiedemann et al., 2009; Lu et al., 2010). NF-κB signaling is involved in cell proliferation, inflammation, migration and apoptosis, and constitutive activation of the NF-κB signaling pathway has been described as a hallmark feature of GBM (Yamamoto et al., 2000; Nozell et al., 2008). Also, an involvement in the cellular mechanisms of radiation and chemotherapy resistance has been proposed (Eyler and Rich, 2008). We thus assumed that Pristimerin exerts its anti-GBM activity via an inhibition of the NF-κB signaling cascade.

Figure 5:
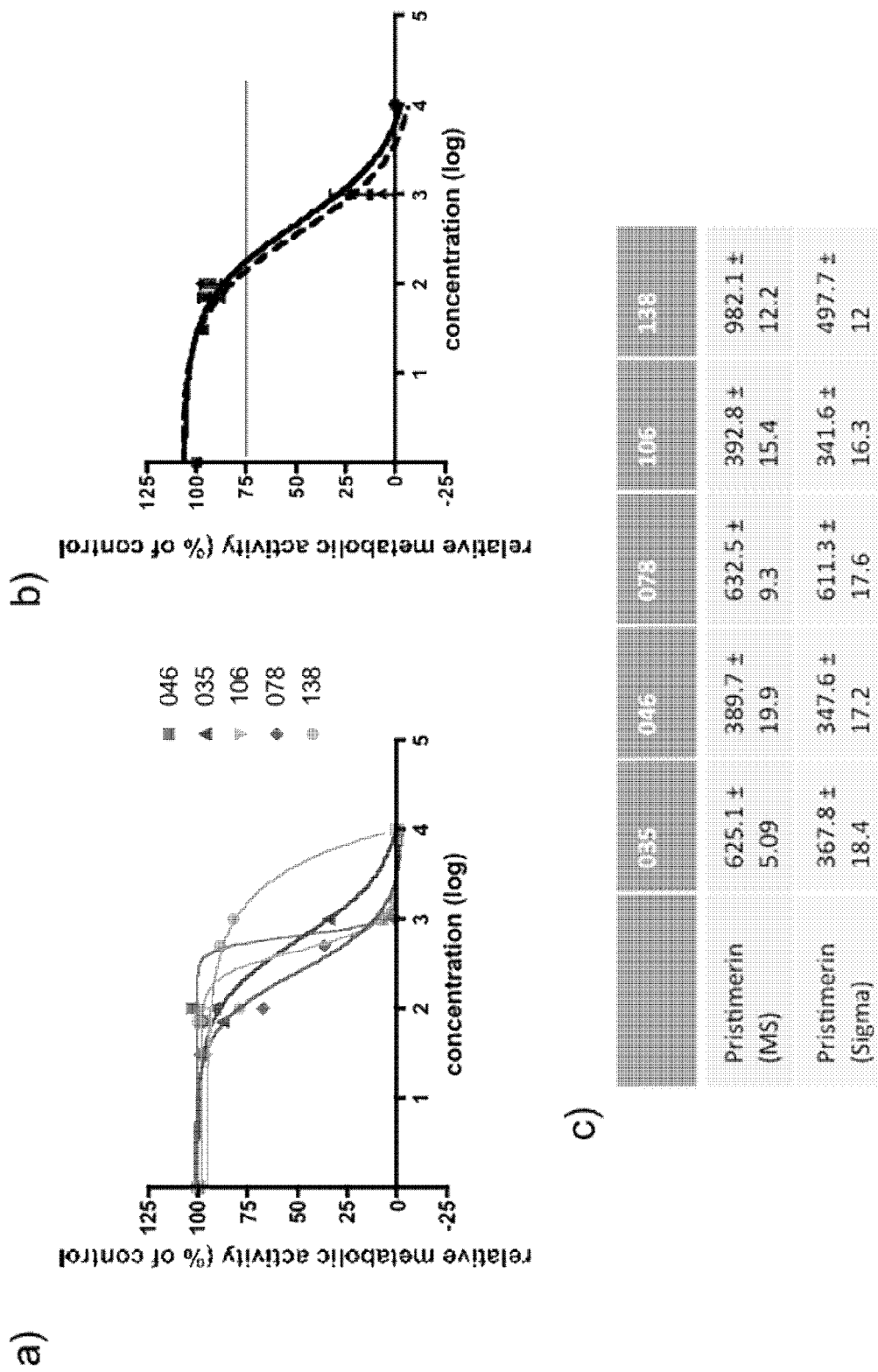
FIG. 5: Pharmacodynamic analysis of Pristimerin on a variety of patient-specific GMB primary cells. The assay was quantified based on AlamarBlue® analysis 5 days post compound application in vitro. (b) Pristimerin purchased from an independent supplier yielded similar results. The median ICM50 of the Microsource compound (solid line) and Sigma compound (dotted line) are 580 and 430 nM respectively. (c) ICM50 values of the patient-specific GBM samples investigated. MS=Microsource, S=Sigma, ICM50=concentration that inhibits the amount of metabolic active cells by 50%. Every data point represents the mean of triplicate analysis.

Pristimerin induces apoptosis in GBM primary cells. The application of pristimerin the four patient-specific GBM cell samples resulted in a very strong reduction of metabolic activity in all cases (023=90%; 035=97%; 046=78%; 106=97%; FIG. 1 bottom). Because the peak plasma concentration of pristimerin is not yet known, we investigated a range of concentrations between 70 nM and 10 µM (FIG. 5). Under these conditions, pristimerin is potently cytotoxic at median $ICM_{50}$'s (half maximal inhibitory concentration of metabolic activity) of approximately 500 nM (FIG. 5a,b, d)

Figure 6:
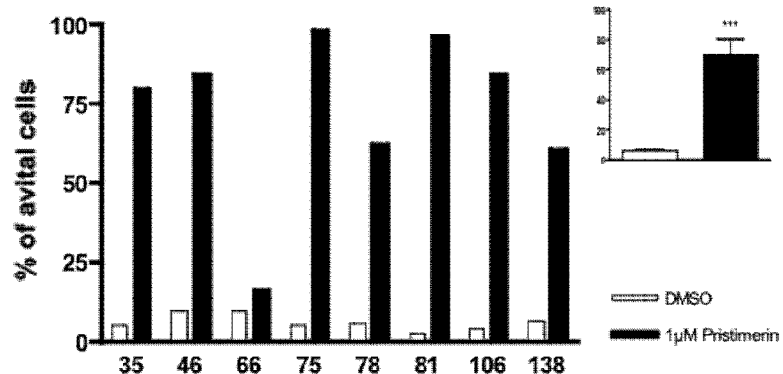
FIG. 6: AnnexinV-based FACS-analysis. Results were obtained 5 days after single-dose application of 1 µM Pristimerin (black bars), or 0.01% DMSO (white bars). The insert displays mean values.

These effects could be validated as compound-specific, based on analysis of Pristimerin purchased from an independent supplier that yielded similar results (Sigma; FIG. 1b). For further experimentation, pristimerin was applied at 1 µM concentrations (FIG. 1c). AnnexinV-based FACS-analysis demonstrated that a 5-day-pristimerin exposure results in a robust induction of apoptosis. In 7 out of 8 investigated patient-specific GBM primary cultures more than 50% of all cells could be classified as avital (FIG. 6; ***p<0.001, compared to their respective DMSO-treated control cells).

Figure 7:
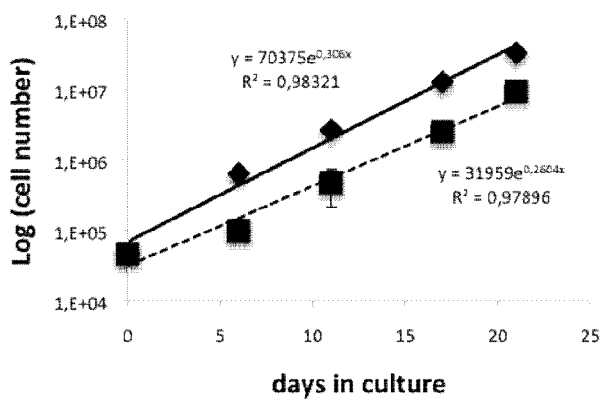
FIG. 7: Growth kinetic analysis (data represent the mean values for patient sample #'s 035, 046, 078, 081 and 106). Under control conditions (0.01% DMSO) GBM primary cells expand linearly on a logarithmic scale (triangles). In every case investigated, decreasing slopes were noted following application of 1 µM pristimerin (squares).

Single-dose application of Pristimerin, however, never resulted in a complete cessation of cellular growth. Cells surviving the application of Pristimerin expand linearly on a logarithmic scale. There is an initial delay of cell growth lasting for a maximum of 10 days. However, thereafter, every patient-specific GBM primary culture we investigated thus far continued to proliferate as well as their respective DMSO-control (FIG. 7).

Figure 8:
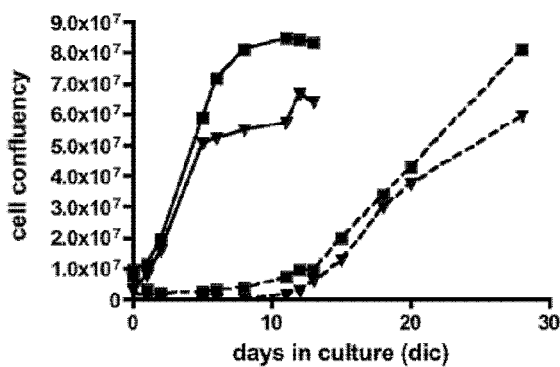
FIG. 8: Long-term monitoring of cellular confluency post application of 1 µM pristimerin (dotted lines) in two independent GBM primary cell culture experiments (035=triangle; 046=squares) (solid line, 0.1% DMSO). Live cell-imaging was performed using the CellaVista system according to its specifications (Roche Diagnostics).

We used the CellaVistasystem (Roche Diagnostics, Mannheim) for monitoring of cell confluency as a surrogate analysis tool. Comparable to the growth kinetic analysis, application of a single dose of Pristimerin resulted in a strong initial decrease of cell confluency. Surviving cells do not take on proliferative activity before 10 days post compound application (FIG. 8).

Figure 9:
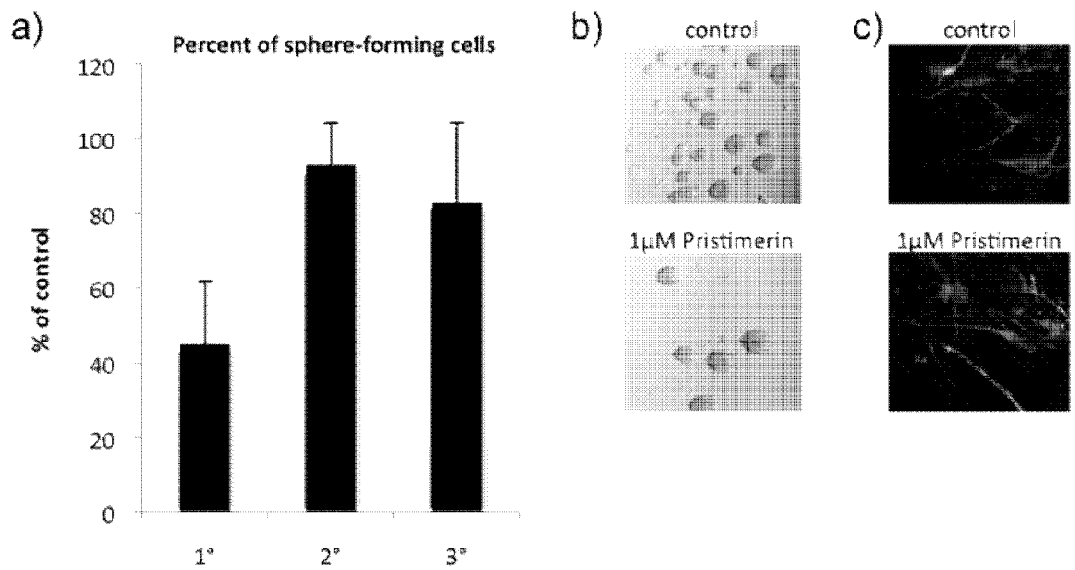
FIG. 9: (a) Relative frequency of primary, secondary and tertiary neurospheres in the NSA after single-dose application of 1 µM pristimerin (data represent mean values for cases 046, 078 and 106). (b) Bright field appearance of control- and treated-primary neurospheres in the NSA. (c) Plating and differentiation of cells from control- and treated-tertiary neurospheres resulted in GFAP-expressing astrocytes and β-tubulin-expressing neurons indicating multipotency of neurosphere-forming cells.

Furthermore, a single dose of pristimerin decreased the frequency of clonogenic, i.e. neurosphere-forming cells by 30-60% (FIG. 9a,b). Depletion of clonogenic cells was never observed at concentrations of 1 mM. Clonogenic cells were always able to selfrenew and form higher-degree neurospheres that gave rise to immature neurons and astrocytes (FIG. 9c). These findings indicate that Pristimerin is not selectively inhibiting GBM cancer stem cells. Pristimerin is rather decreasing the activity of GBM cells with and without stem cell characteristics in a dosage-dependant manner.

Figure 10:
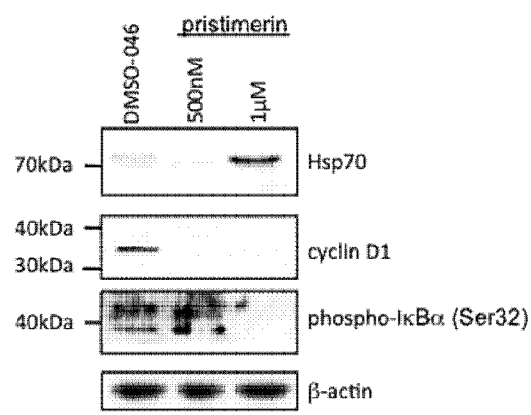
FIG. 10: GBM primary cells (#046) were treated with pristimerin or with 0.01% DMSO for 5 days. Protein extracts were examined by western blot analysis with specific antibodies. To confirm equal protein loading membranes were incubated with a β-actin antibody.

Next, Westernblot analysis was conducted to reveal apoptosis-inducing mechanisms. Data demonstrate that application of Pristimerin results in a loss of a detectable Cyclin D1 and phospho-lκBa signals (FIG. 10). Also, and comparable to studies in myeloma (Tiedemann et al., 2009) a strong induction of heat-shock protein 70 (HSP70)-expression was observed in our samples (FIG. 10).

Figure 11:
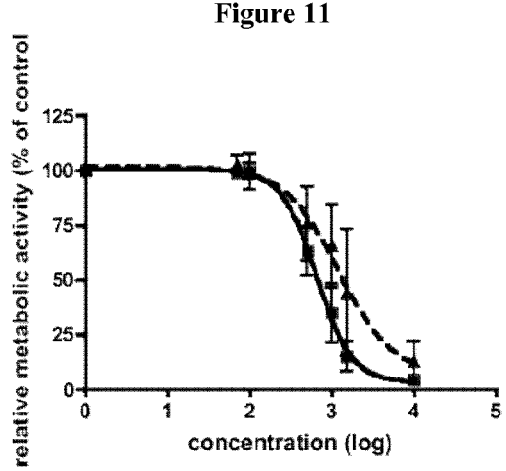
FIG. 11: Inhibition of GBM primary cells under adherent (solid line) vs. non-adherent (dotted line) conditions. Results represent the mean of triplicate-well-analysis for 3 different specimens at each concentration (046, 078, 106)

The GBM-inhibitory activity of Pristimerin was confirmed in 3D culture systems, i.e. non-adherent growth conditions (FIG. 11). Under anchorage-withdrawal, GBM cells form neurospheres, and investigation of their metabolic response patterns indicated a more resistant phenotype. However, GBM cells cultured under these culture conditions can be efficiently inhibited with a single-dose application of Pristimerin (mean $ICM_{50}$=1.1 µM).

Figure 12:
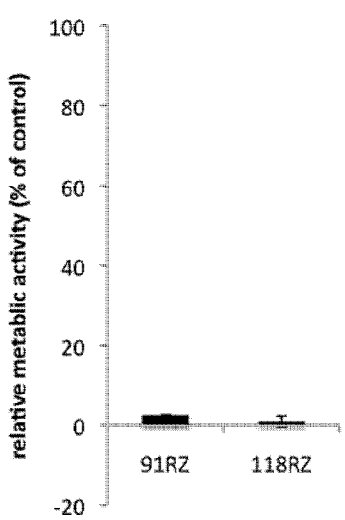
FIG. 12: Relative metabolic activity of two primary cell cultures derived from recurrent GBM tumors after single dose application of 1 mM Pristimerin. AlamarBlue® assay was performed in triplicate wells 5 days after treatment.

Last, because it has been suggested that GBM cells from recurrent disease are responsible for radio- and chemotherapy resistance (Rao et al., 2003), we investigated two respective patient-specific cases (patient #'s 91RZ and 118RZ). In both cases, single-dose application of 1 µM pristimerin resulted in an almost complete deprivation of metabolic activity (FIG. 12).

CONCLUSION

Together, our data establish 31 compounds as potential new candidates for GBM therapy. Among those, 12 compounds were particularly suited for validation experiments (i.e. gambogic acid amide, gambogic acid, pristimerin, epirubicin hydrochloride, emetine, ouabain, ancitabine hydrochloride, quinacrine hydrochloride, niclosamide, amsacrine, aklavine hydrochloride, picropodophyllotoxin). In particular gambogic acid, gambogic acid amide, pristimerin, epirubicin hydrochloride, emetine, and niclosamide are highly efficient anti-GBM therapeutics. The compound Pristimerin represents an excellent new candidate for GBM therapy in settings of primary and recurrent disease. An effective inhibition of human patient-specific GBM cells can be elicited with concentrations of around 1 µM. Pristimerin induces apoptosis in GBM cells with and without stem cell characteristics, it inhibits NF-κB signaling, and it induces the expression of HSp70.

Example 2

Two structurally related molecules, namely Gambogig acid amide (GAA) and Gambogig acid (GA) were chosen for validation. Both, GAA and GA had shown the ability to inhibit the cellular viability of patient-specific primary human glioblastoma cells (pGBMs) below 50% control levels when applied at concentrations of 1 µM.

Figure 13:
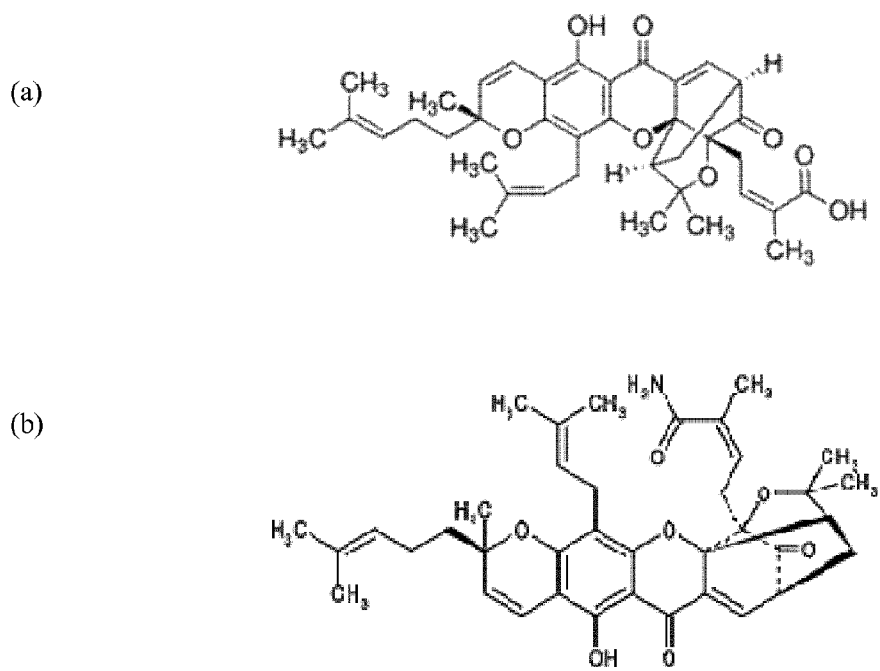
FIG. 13: Structural composition of Gambogic acid (a) and Gambogic acid amide (b) used for this validation study, as provided by the manufacturer. Note: Enzo Life Sciences lists the product on their webpage as TrkA ligand "Gambogig amide".
Figure 15:
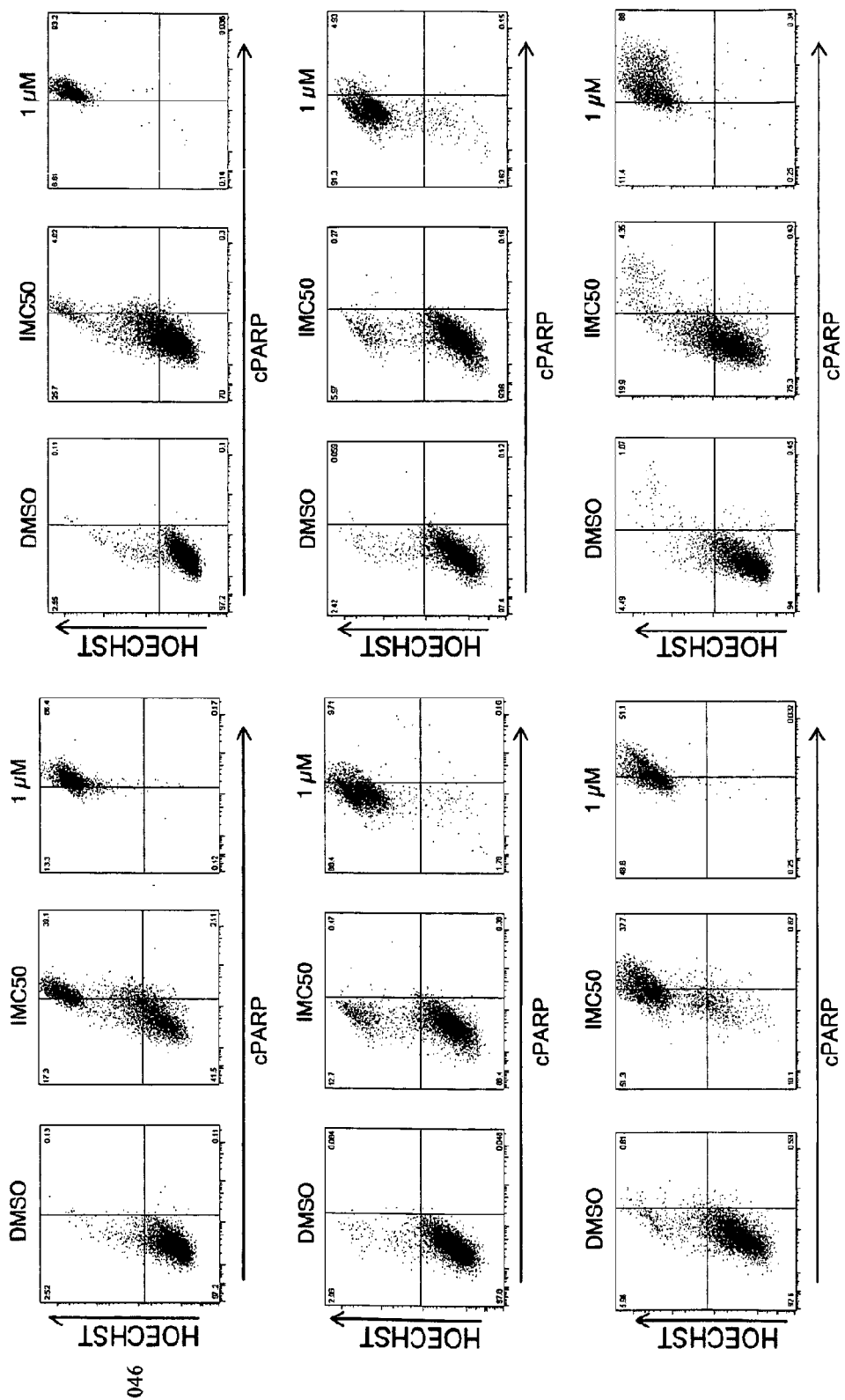
FIG. 15: Cytotoxicity studies. cPARP-based FACS analysis at 5 days following application of DMSO-control, IMC50- or 1 µM-concentrations of the respective compound to pGBMs (#'s indicated). Gambogig acid and Gambogig acid amide appear to confer their cytotoxic effects to a similar degree.

To validate the results obtained from primary screening, these compounds were purchased from independent suppliers (FIG. 13). Pharmacodynamic analysis was conducted by determining the concentrations that decreased the metabolic activity of pGBMs to 50% control levels (IMC50). While comparable dose-response curves were noted, the inhibitory activity of GAA occurred consistently at lower concentrations (FIG. 14), triplicate analysis for each sample). For further analysis, pGBMs were collected at five days following single-dose in vitro application of the respective compound. Cytometric analysis revealed for both compounds strong cytotoxic and only modest cytostatic anti-pGBM effects (FIGS. 15 and 16).

In a next series of experiments we aimed to determine the influence of the compounds on the activity of tumor-initiating cells (TICs). TICs embody a severe functional consequence of intra-tumor heterogeneity as, at least in human glioblastoma, it is anticipated that they are represented by a small subpopulation of stem-like, i.e. self-renewing and multipotent cells (e.g. Sties and Rowitch, 2008; Zhou et al., 2009). In previous work, we established their frequencies in the range from 0.25 to 1% among culture passage 5-10 pGBMs (see Glas et al., 2010). To estimate potential compound-induced alterations to the pool of self-renewing and multipotent cells in pGBMs, the neurosphere assay (NSA) was applied as recently described (Scheffler et al., 2005; Glas et al., 2010). Heterogeneous pGBM samples (#'s 046, 078, 106) were exposed to the compounds, vital cells were collected at day 5, and processed under non-adherent conditions in the NSA (neurosphere assay, see methods). Quantification and differentiation of primary, secondary and tertiary spheres in this assay indicated no GA-induced alteration. By contrast, a single application of GAA surprisingly revealed a considerably reduced frequency of self-renewing, multipotent cells among pGBMs (FIG. 17). Plating and differentiation of cells from DMSO-control or the respective compound pre-treated 3° neurospheres revealed GFAP-expressing astrocytes and betaIII tubulin-expressing neuronal phenotypes. These results indicate an unchanged multipotent capacity of surviving cells.

It was therefore tempting to speculate that only GAA had reduced the fraction of tumorigenic cells among pGBMs. Orthotopic xenotransplantation studies indeed confirmed this assumption (FIG. 18). Statistic analysis implied a significantly increased survival of animals that received GAA pre-treated pGBMs. This effect was not evident in cells pre-treated with GA. Together, these data implied that GAA—in contrast to GA, depleted stem-like cancer cells/TICs effectively, causing a significant decrease of tumor initiating activity among pGBMs.

To further corroborate the cancer stem cell-specific inhibitory activity of GAA, we selected CD133-positive and -negative cell populations from pGBMs (FIG. 19). CD133⁺ cells are known among glioblastoma samples to represent a minority of tumorigenic stem-like phenotypes (Singh et al., 2004). Comparative evaluation of the inhibitory effects induced by GAA and GA on CD133⁺ vs. CD133⁻ pGBM cells confirmed our assumption. Compared to the CD133⁻ population isolated from the same patient sample, the application of GAA led to a significantly stronger reduction of cell growth and viability among CD133⁺ cells (triplicate analysis). A similar selective inhibitory effect could not be revealed for GA.

Together, these data expose GAA as cancer stem cell-specific cytotoxic compound.

Figure 20:
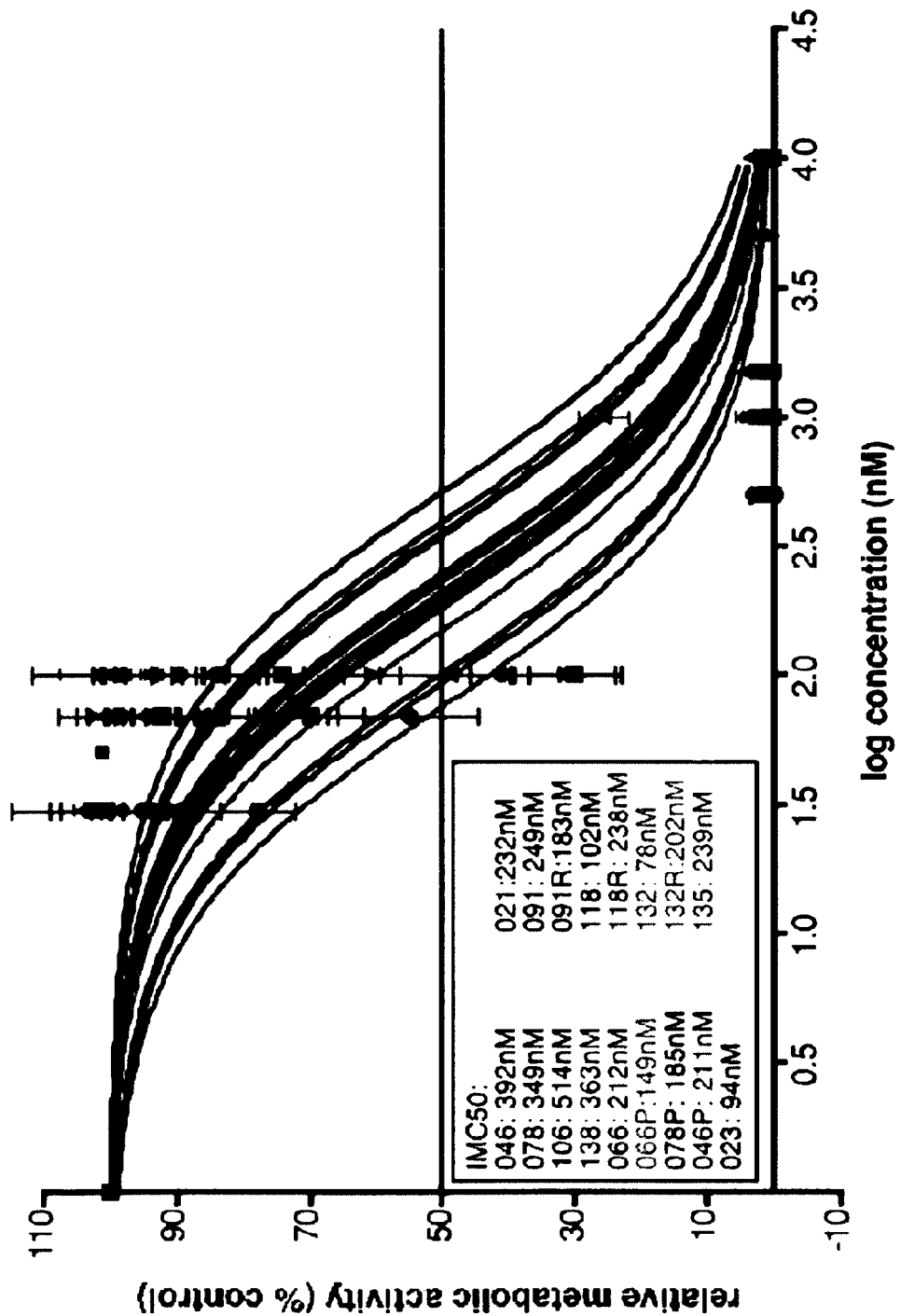
FIG. 20: Gambogic acid amide effectively inhibits cellular viability of a broad spectrum of pGBMs. Pharmocodynamic analysis of 17 pGBMs (#'s indicated) at day 5 following compound exposure (concentrations indicated). The IMC50 values ranged from 78 nM to 514 nM.
Figure 21:
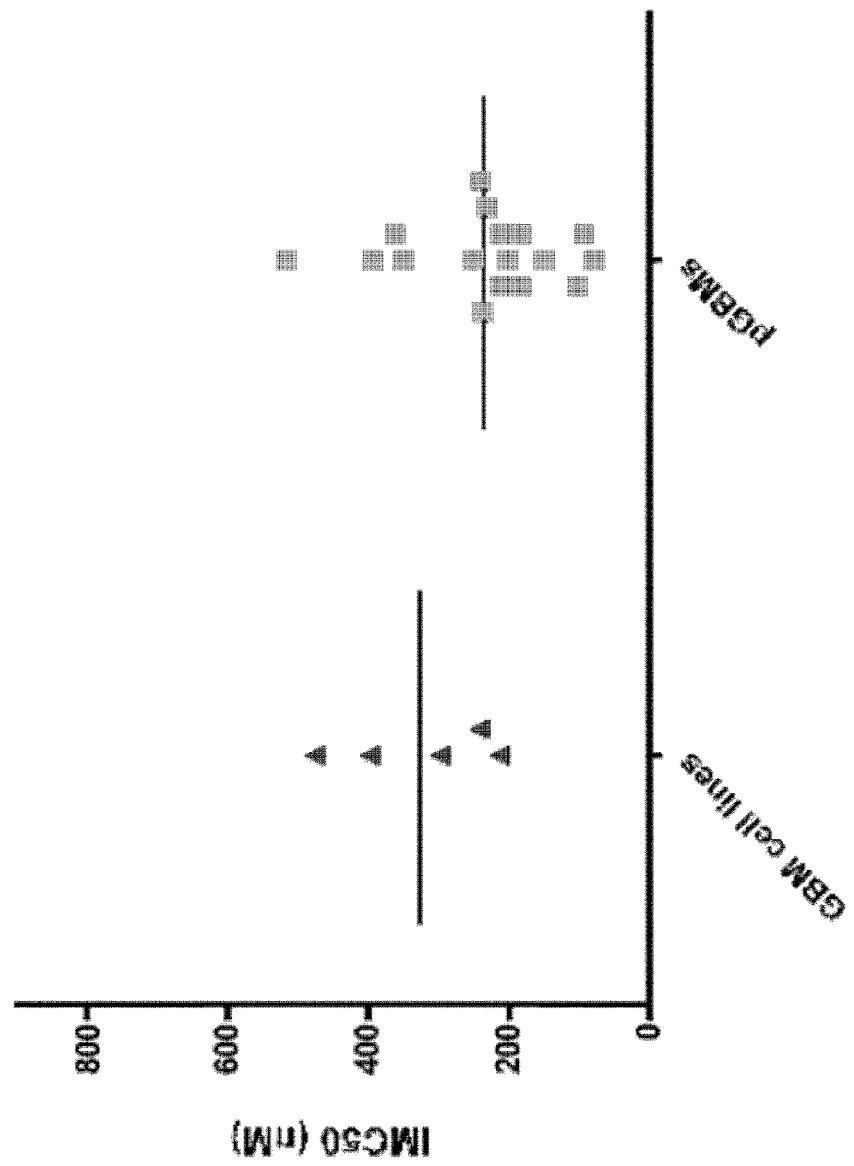
FIG. 21: Stratification of Gambogic acid amide's pharmacodynamic analysis data. (A) Spectrum of IMC50 values representing the concentrations that decrease the metabolic activity to 50% control levels. Data were collected from commercially available glioma/GBM cell lines (blue: LN229, T98G, U87, U138, and U373 cells) and 17 pGBMs. (B) Stratification of pGBM data according to clinically relevant patient subgroups. The graph depicts pair-wise comparisons (shape-coded) of the respective IMC50 values in pGBMs derived from tumor centre vs. periphery, from primary vs. recurrent disease, from MGMT promoter hypermethylated vs. unmethylated specimens, from p53 wildtype (wt) vs. p53 mutated, and from NFKBIA wild type (wt) vs. NFKBIA deleted genotypes. Note that the IMC50 values of Gambogic acid amide do not significantly vary among these subgroups, suggesting a broad applicability of the compound.
Figure 21:
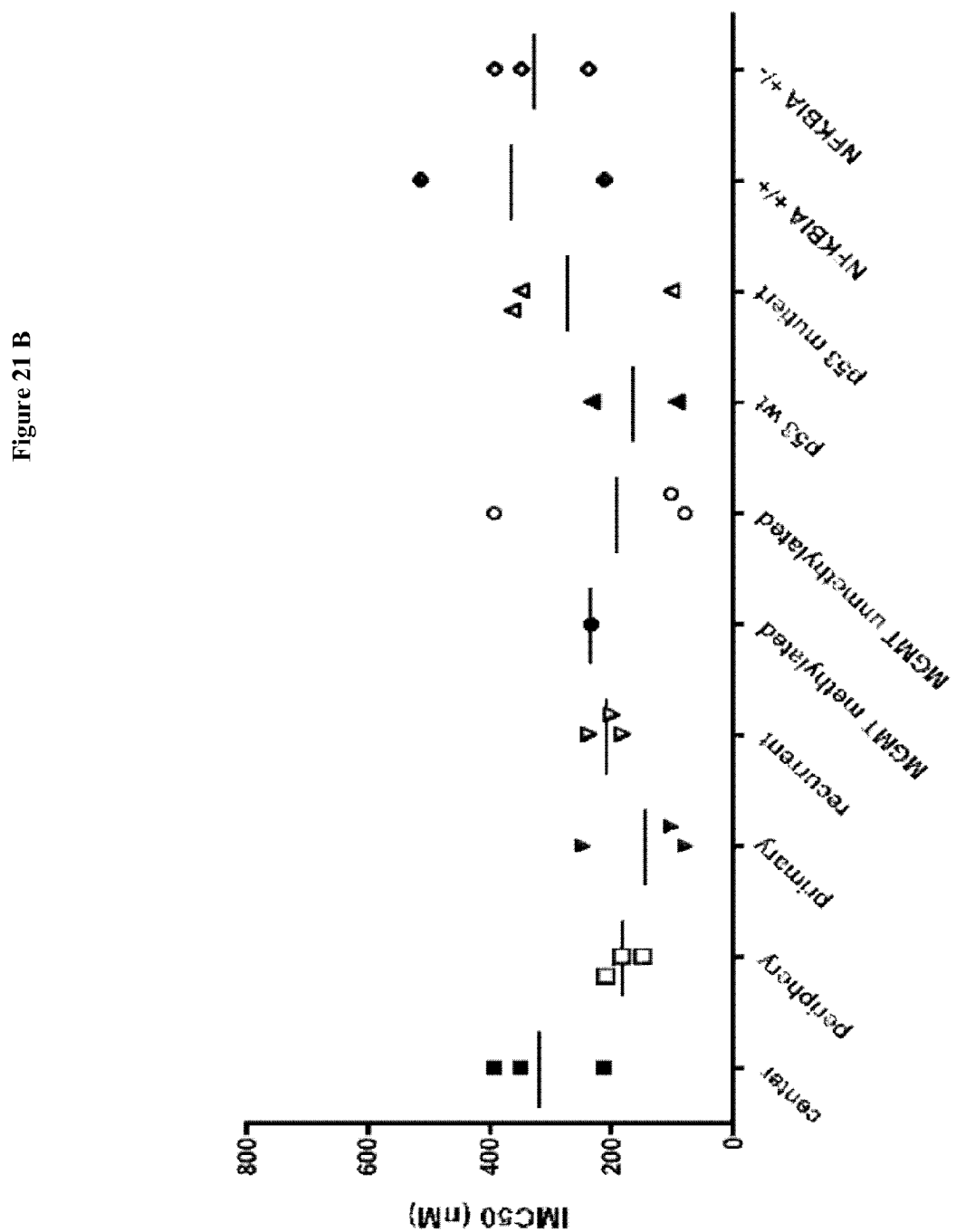

Considering the cellular and genetic diversity that characterizes GBM, we next investigated GAA's pharmacological effect in 17 pGBM samples derived from 11 patients (see Table 2 for list of samples and patient data). The strong inhibitory activity of GAA could be demonstrated in all of the investigated cell lines with IMC50's ranging from 78 nM (#132) to 514 nM (#106) (FIG. 20). Comparable results were obtained from five commercial glioma/GBM cell lines used as a reference (LN229, T98G, U87, U138, and U373, see methods). Next, pair-wise comparison of GAA-pharmacodynamics was performed in pGBMs to stratify results according to key clinical constellations (Bredel et al., 2011; Glas et al., 2010; Simpson et al., 2006; Weller et al., 2010). Glioblastoma samples derived from (i) the tumor center vs. periphery region of the same patient, (ii) primary vs. recurrent disease of the same patient, (iii) MGMT-promoter hypermethylated vs. unmethylated tissue, (iv) p53 wild type vs. p53 mutated samples, as well as from (v) NFKBIA wild type vs. NFKBIA deleted genotypes. GAA appeared to inhibit all of these samples to a similar degree (FIG. 21).

Together, these data confirmed and validated our primary screening results, portraying GAA as a highly effective cytotoxic anti-pGBM compound, preferentially targeting tumorigenic, cancer stem-like phenotypes.

Reagents

The following reagents were purchased for this study: AlamarBlue®, prodidiumiodide, LIVE/DEAD® fixable dead cell stain Kit and Hoechst33342 (Life Technologies); gambogic acid (Sigma-Aldrich); gambogic acid amide (Enzo Life Sciences).

Mice

The Ethical Committee of the University of Bonn, Medical Centre approved all studies involving animals. Rag2Il2rg$^{-/-}$ mice were acquired from Taconic Farm Inc., contractor of the National Institute of Allergy and Infectious Diseases' investigators (Cao et al., 1995).

Tissue Samples

Tumor tissue derived from GBM surgery. Patient characteristics are detailed in Supplemental Table 1. The local Ethics committees approved the studies, respectively; all patients provided informed consent. Tissue diagnosis and grading based on the current classification of the World Health Organization (Louis et al., 2007) and was confirmed by two independent neuropathologists at the Department of Neuropathology, University of Bonn Medical Centre (the National Reference Center of Neuropathology).

Tissue Handling and Culture of Primary Cells

Handling of fresh biopsy samples and derivation of pGBMs (Glas et al., 2010) were performed as described recently. Media conditions for pGBM samples are described in (Glas et al., 2010; Lee et al., 2006). Data were generated from culture passages 7 to 10.

TABLE 2

| Patient (case#) | Diagnosis | Sex | Age | Histology | RPA Class | Primary therapy | PFS | OS | MGMT status |
|---|---|---|---|---|---|---|---|---|---|
| 021 | new | m | 78 | GBM | V | R, RT/TMZ, 2 × TMZ (5/28) | 4 | 12 | unmet |
| 023 | new | f | 79 | GBM | V | RA | NA | 9 | meth |
| 046D | new | m | 76 | GBM | IV | RB | 1 | 1 | unmet |
| 066D | new | f | 69 | GBM | IV | R, RT/TMZC | 2 | 2 | unmet |
| 078D | new | m | 52 | GBM | IV | R, RT/TMZ, 2 × TMZ (5/28) | 5 | 10+ | unmet |
| 091E | new | m | 52 | GBM | IV | R, RT/TMZ, 4 × TMZ (5/28) | 7 | 10 | unmet |
| 106 | new | f | 68 | GBM | IV | R, RT/TMZ, 1 × TMZ (5/28) | 5 | 5+ | unmet |
| 118E | new | m | 63 | GBM | IV | R, RT/TMZ, 4 × TMZ (5/28) | 7 | 9 | unmet |
| 132E | new | m | 75 | GBM | IV | R, RT/TMZ, 4 × TMZ (5/28) | 7 |  | n.d. |
| 135 | new | m | 41 | GBM | IV | R, RT/TMZC | 8 | 9 | n.d. |
| 138 | new | w | 54 | GBM | IV | R, RT/TMZ, 5 × TMZ (5/28) | 10 | 14+ | unmet |

Table 2: List of patients and tissue specimens investigated in this study.
A: Patient denied further treatment;
B: Postoperative complications;
C: Discontinuation of therapy due to clinical deterioration;
D: isolated cells from paired GBM biopsy samples representing centre and periphery of the same, respective brain tumor;
E: isolated cells from GBM biopsy samples representing primary and recurrent disease from the same patient;
R: Tumor resection;
RT: Standard radiotherapy;
RT/TMZ: RT plus continous daily temozolomide (concomitant);
TMZ: Temozolomide (5/28: days 1 to 5 out of a 28-day cycle);
PFS: Progression-free survival;
OS: Overall survival;
meth: methylated MGMT promoter;
unmet: unmethylated MGMT promoter Pharmacodynamic Analysis For pharmacodynamic analysis, $5\times10^4$ cells were plated in 12-well-plates at 24 hours before application of compound-series. AlamarBlue®-based analysis was conducted at 5 days post treatment. Experiments were performed in triplicates. IMC50 was defined as the compound concentration that reduced the metabolic activity by 50% compared to control conditions and determined via data analysis in GraphPad Prism 4.0.

Cell Cycle Analysis

Cells ($5\times10^4$ per well) were grown in 12-well plates, and collected after treatment at times indicated. Cells were re-suspended in phosphate-buffered saline (PBS), fixed with ice-cold methanol and incubated for a minimum of 24 hours at 4° C. Cell pellets were collected by centrifugation and re-suspended in PBS solution, containing 50 µg/ml propidium iodide and 50 µg/ml RNase. Following incubation for 30 min at 37° C., cells were analyzed for DNA content using a FACS caliber flow cytometer (BD Bioscience).

cPARP-Based FACS Analysis $1\times10^5$ cells were collected at 5 days following compound application, settled by centrifugation, re-suspended in 100 µl LIVE/DEAD fixable dead Stain FarRed and incubated for 30 minutes at 4° C. Cells were then fixed in ice-cold 4% (w/v) paraformaldehyde in PBS for 10 minutes and permeabilized with 0.5% Triton X-100 for 5 minutes. The cell suspension was then stained with a FITC-coupled cPARP antibody (BD Bioscience; 1:5 dilution) for 30 minutes at room temperature. To distinguish between living and dead cells, labeling with 1.2 µg/ml Hoechst 33258 was used. Expression was determined using standard conditions in a LSRII equipped with FACSDiva Software (BD Bioscience). 20.000 cells were counted per measurement.

Neurosphere Assay

The neurosphere assay was performed to estimate the frequency of self-renewing clonogenic cells according to established protocols (Glas et al., 2010; Scheffler et al., 2005). Neurospheres were quantified at 21 days in culture, triturated to a single cell suspension, and re-plated for analysis of the secondary and tertiary neurospheres. Multipotency was determined by plating a representative fraction of 3° neurospheres onto laminin/poly-L-ornithine coated glass coverslips allowing differentiation for 2-3 weeks before fixation in 4% paraformaldehyde (PFA).

Fluorescence Analysis

Immunofluorescence analysis was performed on PFA-fixed samples according to standard protocols (Scheffler et al., 2005) using antibodies against bIII tubulin (Promega; monoclonal mouse, 1:1000) and GFAP (DAKO, polyclonal rabbit, 1:600). Cell nuclei were visualized with DAPI (Sigma).

Separation of CD133+ and CD133− Cells

For fluorescence-activated cell separation (FACS), cells were stained with CD133/2-PE or with CD133/2-APC (both 1:20; Miltenyi Biotech) and sorted on a BD FACS DiVa Cell Sorter (Becton Dickinson).

Tumor Xenograft Experiments

Cells were harvested, counted and re-suspended in 0.1% DNase/PBS. Cellular viability was confirmed via trypan blue exclusion. $10^6$ DMSO-control-, gambogic acid or gambogic acid amide-pretreated pGBMs were injected stereotactically into the striatum of 12 week old Rag2Il2rg$^{-/-}$ mice (0.8 mm anterior, 2 mm lateral, 3 mm deep). Mice were monitored daily and euthanized upon presentation with signs of distress/neurological symptoms or significant weight loss. For subsequent histological analysis, brains were removed, cryoprotected, and serially cut on a cryostat (Leica) at 20 µm thickness. Every fifth section underwent routine H&E staining for histological analysis of tumor formation.

REFERENCES

Avilla, J.; Teixido, A.; Velazquez, C.; Alvarenga, N.; Ferro, E. and Canela, R. (2000): Insecticidal activity of Maytenus species (Celastraceae) nortriterpene quinone methides against codling moth, *Cydia pomonella* (L.) (Lepidoptera: tortricidae), J Agric Food Chem (vol. 48), No. 1, pp. 88-92.

Beier, D.; Rohrl, S.; Pillai, D. R.; Schwarz, S.; Kunz-Schughart, L. A.; Leukel, P.; Proescholdt, M.; Brawanski, A.; Bogdahn, U.; Trampe-Kieslich, A.; Giebel, B.; Wischhusen, J.; Reifenberger, G.; Hau, P. and Beier, C. P. (2008): Temozolomide preferentially depletes cancer stem cells in glioblastoma, Cancer Res (vol. 68), No. 14, pp. 5706-15.

Bredel, M., Scholtens, D. M., Yadav, A. K., Alvarez, A. A., Renfrow, J. J., Chandler, J. P., Yu, I. L., Carro, M. S., Dai, F., Tagge, M. J., et al. 2011. NFKBIA deletion in glioblastomas. N Engl J Med 364:627-637.

Buffa Filho, W.; Corsino, J.; Bolzani da, S. V.; Furlan, M.; Pereira, A. M. and Franca, S. C. (2002): Quantitativedetermination for cytotoxic Friedo-nor-oleanane derivatives from five morphological types of *Maytenus ilicifolia* (Celastraceae) by reverse-phase high-performance liquid chromatography, Phytochem Anal (vol. 13), No. 2, pp. 75-8.

Cao, X., Shores, E. W., Hu-Li, J., Anver, M. R., Kelsall, B. L., Russell, S. M., Drago, J., Noguchi, M., Grinberg, A., Bloom, E. T., et al. 1995. Defective lymphoid development in mice lacking expression of the common cytokine receptor gamma chain. *Immunity* 2:223-238.

Chalmers, A. J. (2007): Radioresistant glioma stem cells-therapeutic obstacle or promising target?, DNA Repair (Amst) (vol. 6), No. 9, pp. 1391-4.

Chang, F. R.; Hayashi, K.; Chen, I. H.; Liaw, C. C.; Bastow, K. F.; Nakanishi, Y.; Nozaki, H.; Cragg, G. M.; Wu, Y. C. and Lee, K. H. (2003): Antitumor agents. 228. five new agarofurans, Reissantins A-E, and cytotoxic principles from *Reissantia buchananii*, J Nat Prod (vol. 66), No. 11, pp. 1416-20.

Dirks, P. B. (2008): Brain tumor stem cells: bringing order to the chaos of brain cancer, J Clin Oncol (vol. 26), No. 17, pp. 2916-24.

Dirsch, V. M.; Kiemer, A. K.; Wagner, H. and Vollmar, A. M. (1997): The triterpenoid quinonemethide pristimerin inhibits induction of inducible nitric oxide synthase in murine macrophages, Eur J Pharmacol (vol. 336), No. 2-3, pp. 211-7.

Figueiredo, J. N.; Raz, B. and Sequin, U. (1998): Novel quinone methides from *Salacia kraussii* with in vitro antimalarial activity, J Nat Prod (vol. 61), No. 6, pp. 718-23.

Glas, M.; Rath, B. H.; Simon, M.; Reinartz, R.; Schramme, A.; Trageser, D.; Eisenreich, R.; Leinhaas, Keller, M.; Schildhaus, H. U.; Garbe, S.; Steinfarz, B.; Pietsch, T.; Steindler, D. A.; Schramm, J.; Herrlinger, U.; Brustle, and Scheffler, B. Residual tumor cells are unique cellular targets in glioblastoma, Ann Neurol (vol. 68), No. 2, pp. 264-9.

Goetz, A. K.; Scheffler, B.; Chen, H. X.; Wang, S.; Suslov, O.; Xiang, H.; Brustle, O.; Roper, S. N. and Steindler, D. A. (2006): Temporally restricted substrate interactions direct fate and specification of neural precursors derived from embryonic stem cells, Proc Natl Acad Sci USA (vol. 103), No. 29, pp. 11063-8.

Honda, T.; Rounds, B. V.; Bore, L.; Favaloro, F. G., Jr.; Gribble, G. W.; Suh, N.; Wang, Y. and Spor, M. (1999): Novel synthetic oleanane triterpenoids: a series of highly active inhibitors of nitric oxide production in mouse macrophages, Bioorg Med Chem Lett (vol. 9), No. 24, pp. 3429-34.

Ji, Y.; Lee, H. J.; Goodman, C.; Uskokovic, M.; Liby, K.; Sporn, M. and Suh, N. (2006): The synthetic triterpenoid CDDO-imidazolide induces monocytic differentiation by activating the Smad and ERK signaling pathways in HL60 leukemia cells, Mol Cancer Ther (vol. 5), No. 6, pp. 1452-8.

Lee, J.; Kotliarova, S.; Kotliarov, Y.; Li, A.; Su, Q.; Donin, N. M.; Pastorino, S.; Purow, B. W.; Christopher, N.; Zhang, W.; Park, J. K. and Fine, H. A. (2006): Tumor stem cells derived from glioblastomas cultured in bFGF and EGF more closely mirror the phenotype and genotype of primary tumors than do serum-cultured cell lines, Cancer Cell (vol. 9), No. 5, pp. 391-403.

Louis, D. N.; Ohgaki, H.; Wiestler, O. D.; Cavenee, W. K.; Burger, P.; Jouvet, A.; Scheithauer, B. W. and Kleihues, P. (2007): The 2007 WHO classification of tumours of the central nervous system, Acta Neuropathol (vol. 114), No. 2, pp. 97-109.

Lu, Z.; Jin, Y.; Chen, C.; Li, J.; Cao, Q. and Pan, J. Pristimerin induces apoptosis in imatinib-resistant chronic myelogenous leukemia cells harboring T315I mutation by blocking NF-kappaB signaling and depleting Bcr-Abl, Mol Cancer (vol. 9), p. 112.

Luo, D. Q.; Wang, H.; Tian, X.; Shao, H. J. and Liu, J. K. (2005): Antifungal properties of pristimerin and celastrol isolated from *Celastrus hypoleucus*, Pest Manag Sci (vol. 61), No. 1, pp. 8590.

Niampoka, C.; Suttisri, R.; Bavovada, R.; Takayama, H. and Aimi, N. (2005): Potentially cytotoxic triterpenoids from the root bark of *Siphonodon celastrineus* Griff, Arch Pharm Res (vol. 28), No. 5, pp. 546-9.

Pardal, R.; Clarke, M. F. and Morrison, S. J. (2003): Applying the principles of stem-cell biology to cancer, Nat Rev Cancer (vol. 3), No. 12, pp. 895-902.

Pollard, S. M.; Yoshikawa, K.; Clarke, I. D.; Danovi, D.; Stricker, S.; Russell, R.; Bayani, J.; Head, R.; Lee, M.; Bernstein, M.; Squire, J. A.; Smith, A. and Dirks, P. (2009): Glioma stem cellines expanded in adherent culture have tumor-specific phenotypes and are suitable for chemical and genetic screens, Cell Stern Cell (vol. 4), No. 6, pp. 568-80.

Rao, J. S. (2003): Molecular mechanisms of glioma invasiveness: the role of proteases, Nat Rev Cancer (vol. 3), No. 7, pp. 489-501.

Sassa, H.; Kogure, K.; Takaishi, Y. and Terada, H. (1994): Structural basis of potent antiperoxidation activity of the triterpene celastrol in mitochondria: effect of negative membrane surface charge on lipid peroxidation, Free Radic Biol Med (vol. 17), No. 3, pp. 201-7.

Scheffler, B.; Walton, N. M.; Lin, D. D.; Goetz, A. K.; Enikolopov, G.; Roper, S, N. and Steindler, D. A. (2005): Phenotypic and functional characterization of adult brain neuropoiesis, Proc Natl Acad Sci USA (vol. 102), No. 26, pp. 9353-8.

Simpson, L., and Galanis, E. 2006. Recurrent glioblastoma multiforme: advances in treatment and promising drug candidates. *Expert Rev Anticancer Ther* 6:1593-1607.

Singh, S. K.; Hawkins, C.; Clarke, I. D.; Squire, J. A.; Bayani, J.; Hide, T.; Henkelman, R. M.; Cusimano, M. D. and Dirks, P. B. (2004): Identification of human brain tumour initiating cells, Nature (vol. 432), No. 7015, pp. 396-401.

Stiles, C. D., and Rowitch, D. H. 2008. Glioma stem cells: a midterm exam. *Neuron* 58:832-846.

Stupp, R.; Mason, W. P.; van den Bent, M. J.; Weller, M.; Fisher, B.; Taphoorn, M. J.; Belanger, K.; Brandes, A. A.; Marosi, C.; Bogdahn, U.; Curschmann, J.; Janzer, R. C.; Ludwin, S. K.; Gorlia, T.; Allgeier, A.; Lacombe, D.; Cairncross, J. G.; Eisenhauer, E. and Mirimanoff, R. O. (2005): Radiotherapy plus concomitant and adjuvant temozolomide for glioblastoma, N Engl J Med (vol. 352), No. pp. 987-96.

Suh, N.; Roberts, A. B.; Birkey Reffey, S.; Miyazono, K.; Itoh, S.; ten Dijke, P.; Heiss, E. H.; Place, A. E.; Risingsong, R.; Williams, C. R.; Honda, T.; Gribble, G. W. and Sporn, M. B. (2003): Synthetic triterpenoids enhance transforming growth factor beta/Smad signaling, Cancer Res (vol. 63), No. 6, pp. 1371-6.

Suh, W. S.; Kim, Y. S.; Schimmer, A. D.; Kitada, S.; Minden, M.; Andreeff, M.; Suh, N.; Sporn, M. and Reed, J. C. (2003): Synthetic triterpenoids activate a pathway for apoptosis in AML cells involving downregulation of FLIP and sensitization to TRAIL, Leukemia (vol. 17), No. 11, pp. 2122-9.

Tiedemann, R. E.; Schmidt, J.; Keats, J. J.; Shi, C. X.; Zhu, Y. X.; Palmer, S. E.; Mao, X.; Schimmer, A. D. and Stewart, A. K. (2009): Identification of a potent natural triterpenoid inhibitor of proteosome chymotrypsin-like activity and NF-kappaB with antimyeloma activity in vitro and in vivo, Blood (vol. 113), No. 17, pp. 4027-37.

Weller, M., Stupp, R., Reifenberger, G., Brandes, A. A., van den Bent, M. J., Wick, W., and Hegi, M. E. 2010. MGMT promoter methylation in malignant gliomas: ready for personalized medicine? *Nat Rev Neurol* 6:39-51.

Wiechen, K.; Diatchenko, L.; Agoulnik, A.; Scharff, K. M.; Schober, H.; Arlt, K.; Zhumabayeva, B.; Siebert, P. D.; Dietel, M.; Schafer, R. and Sers, C. (2001): Caveolin-1 is down-regulated in human ovarian carcinoma and acts as a candidate tumor suppressor gene, Am J Pathol (vol. 159), No. 5, pp. 1635-43.

Yamamoto, M.; Fukushima, T.; Hayashi, S.; Ikeda, K.; Tsugu, H.; Kimura, H.; Soma, G. and Tomonaga, M. (2000): Correlation of the expression of nuclear factor-kappa B, tumor necrosis factor receptor type 1 (TNFR 1) and c-Myc with the clinical course in the treatment of malignant astrocytomas with recombinant mutant human tumor necrosis factor-alpha (TNF-SAM2), Anticancer Res (vol. 20), No. 1C, pp. 611-8.

Zhou, B. B., Zhang, H., Damelin, M., Geles, K. G., Grindley, J. C., and Dirks, P. B. 2009. Tumour-initiating cells: challenges and opportunities for anticancer drug discovery. *Nat Rev Drug Discov* 8:806-823.

The invention claimed is:

1. A method of treating glioblastoma, comprising administering a compound according to the formula,

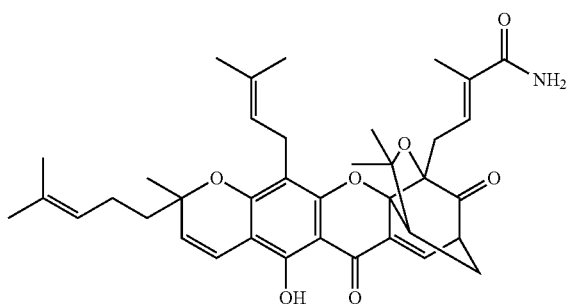 [SMILES: CC(C)=CCCC1(C)C=Cc2c(O)c3c(c(CC=C(C)C)c2O1)OC12C(=CC4CCC1C(C)(C)OC2(C/C=C(\C)C(N)=O)C4=O)C3=O]

or salts thereof.

2. The method of claim 1, wherein the glioblastoma to be treated is selected from the group consisting of primary glioblastoma, recurrent glioblastoma, glioblastoma with increased methylation of the promoter of the gene 06-Methylguanin-Methyltransferase (MGMT), glioblastoma without increased methylation of the promoter of MGMT, glioblastoma with mutated p53, glioblastoma without mutated p53, glioblastoma with alterations of the gene encoding kappa light polypeptide gene enhancer in B-cells inhibitor (NFKBIA), glioblastoma without alterations of the gene encoding NFKBIA, glioblastoma with alterations of the gene encoding epidermal growth factor receptor (EGFR), glioblastoma without alterations of the gene encoding EGFR, glioblastoma with alterations of the gene encoding platelet-derived growth factor receptor (PDGFRA), glioblastoma without alterations of the gene encoding PDGFRA, glioblastoma with alterations of the gene encoding isocitrate dehydrogenase 1 (IDHI), glioblastoma without alterations of the gene encoding IDHI, glioblastoma with alterations of the gene encoding neurofibromatosis type 1 (NF1) and glioblastoma without alterations of the gene encoding NF1.

3. The method of claim 1, wherein the glioblastoma comprises cells overexpres sing or expressing a gene selected from the group consisting of CD133, ATP-binding cassette sub-family G member 2 (ABCG2), aldehyde dehydrogenase 1 (ALDH1A1), musashi homolog 1 (MSI-1), Nestin and sex determining region Y-box 2 (SOX-2).

4. The method of claim 1, wherein said glioblastoma comprises a subset of stem-like cells.

5. The method of claim 1, wherein said compound delays cell growth of said glioblastoma cells for up to 10 days after administration.

6. A method for inhibiting glioblastoma cells, said method comprising contacting said glioblastoma cells with a pharmaceutical composition comprising a compound according to the formula

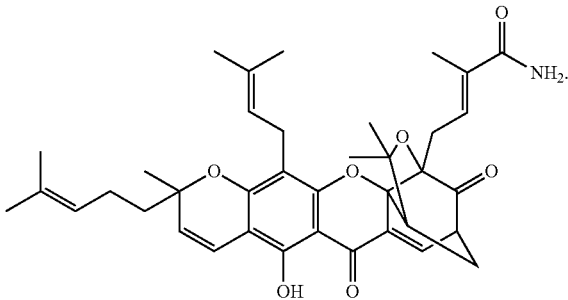 [SMILES: CC(C)=CCCC1(C)C=Cc2c(O)c3c(c(CC=C(C)C)c2O1)OC12C(=CC4CCC1C(C)(C)OC2(C/C=C(\C)C(N)=O)C4=O)C3=O]

7. The method of claim 6, wherein the glioblastoma to be treated is selected from the group consisting of primary glioblastoma, recurrent glioblastoma, glioblastoma with increased methylation of the promoter of the gene 06-Methylguanin-Methyltransferase (MGMT), glioblastoma without increased methylation of the promoter of MGMT, glioblastoma with mutated p53, glioblastoma without mutated p53, glioblastoma with alterations of the gene encoding kappa light5 alterations of the gene encoding NFKBIA, glioblastoma with alterations of the gene encoding epidermal growth factor receptor (EGFR), glioblastoma without alterations of the gene encoding EGFR, glioblastoma with alterations of the gene encoding platelet-derived growth factor receptor (PDGFRA), glioblastoma without alterations of the gene encoding PDGFRA, glioblastoma with alterations of the gene encoding isocitrate dehydrogenase 1 (IDHI), glioblastoma without alterations of the gene encoding IDHI, glioblastoma with alterations of the gene encoding neurofibromatosis type 1 (NF1) and glioblastoma without alterations of the gene encoding NF1.

8. The method of claim 6, wherein the glioblastoma comprises cells overexpres sing or expressing a gene selected from the group consisting of CD133, ATP-binding cassette sub-family G member 2 (ABCG2), aldehyde dehydrogenase 1(ALDH1A1), musashi homolog 1 (MSI-1), Nestin and sex determining region Y-box 2 (SOX-2).

9. A method of treating glioblastoma, comprising administering to a patient having glioblastoma a pharmaceutical composition, said pharmaceutical composition comprising a compound according to the formula

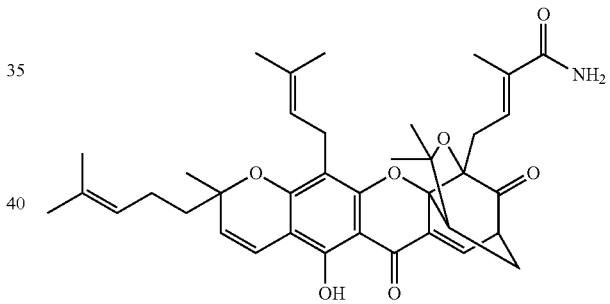

and further comprising at least one further compound with anticancer-activity.

10. The method of claim 9, wherein the at least one further compound is temozolomide or a salt thereof.

11. A method for determining if treatment with a compound according to the formula

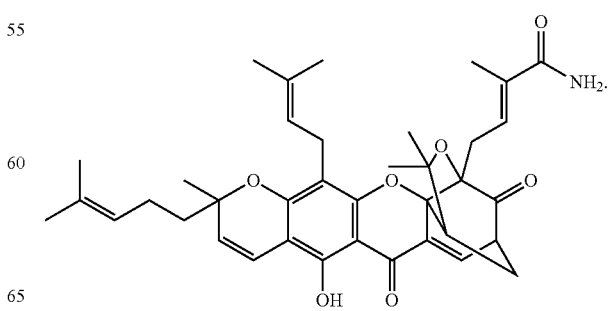

is suitable for a patient comprising the steps of
a) providing a sample of tumor tissue or tumor cells of the patient;
b) determining whether said compound is capable of killing cells of said tumor tissue or said tumor cells, wherein said compound is suitable for treating said patient if it is capable of killing cells of said tumor tissue or said tumor cells.

\* \* \* \* \*